United States Patent
Gemba et al.

(10) Patent No.: US 9,376,470 B2
(45) Date of Patent: *Jun. 28, 2016

(54) POLYPEPTIDE HAVING ANGIOGENESIS-INDUCING ACTIVITY AND ANTIBACTERIAL ACTIVITY, AND USE THEREOF FOR MEDICAL PURPOSES

(75) Inventors: Takefumi Gemba, Kawanishi (JP); Hideki Tomioka, Minoh (JP); Ryoko Sata, Ibaraki (JP); Nao Tamura, Suita (JP); Akito Maeda, Kyoto (JP); Toshihide Kanamori, Ikeda (JP); Yoshimi Saito, Toyonaka (JP); Shintaro Komaba, Ikeda (JP); Ryuichi Morishita, Suita (JP)

(73) Assignee: FunPep Inc., Tokyo (JP)

( * ) Notice: Subject to any disclaimer, the term of this patent is extended or adjusted under 35 U.S.C. 154(b) by 710 days.

This patent is subject to a terminal disclaimer.

(21) Appl. No.: 13/131,796

(22) PCT Filed: Nov. 27, 2009

(86) PCT No.: PCT/JP2009/070035
§ 371 (c)(1),
(2), (4) Date: Nov. 28, 2011

(87) PCT Pub. No.: WO2010/061915
PCT Pub. Date: Jun. 3, 2010

(65) Prior Publication Data
US 2012/0122766 A1 May 17, 2012

(30) Foreign Application Priority Data
Nov. 28, 2008 (JP) ................. 2008-303502

(51) Int. Cl.
*C07K 7/04* (2006.01)
*C07K 14/00* (2006.01)
*C07K 14/515* (2006.01)
*A61K 38/00* (2006.01)

(52) U.S. Cl.
CPC ............. *C07K 14/001* (2013.01); *C07K 14/515* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,939,224 A * | 7/1990 | Musso et al. | 530/324 |
| 7,452,856 B2 | 11/2008 | Nagaoka et al. | |
| 7,674,771 B2 | 3/2010 | Yoshida et al. | |
| 7,807,176 B2 | 10/2010 | Nishikawa et al. | |
| 7,964,556 B1 | 6/2011 | Kobayashi et al. | |
| 8,012,749 B2 | 9/2011 | Yano et al. | |
| 8,470,765 B2 | 6/2013 | Gemba et al. | |
| 8,969,311 B2 | 3/2015 | Gemba et al. | |
| 2005/0214321 A1 | 9/2005 | Rasochova et al. | |
| 2006/0122122 A1 | 6/2006 | Kobayashi et al. | |
| 2007/0032361 A1 | 2/2007 | Yoshida et al. | |
| 2007/0281888 A1 | 12/2007 | Nishikawa et al. | |
| 2008/0025962 A1 | 1/2008 | Hayashi et al. | |
| 2008/0069849 A1 | 3/2008 | Schmidtchen et al. | |
| 2009/0143319 A1 | 6/2009 | Gemba et al. | |
| 2009/0149632 A1 | 6/2009 | Nagaoka et al. | |
| 2010/0167390 A1 | 7/2010 | Nakajima et al. | |
| 2012/0052104 A1 | 3/2012 | Gemba | |
| 2012/0172287 A1 | 7/2012 | Gemba | |
| 2015/0133365 A1 | 5/2015 | Gemba et al. | |

FOREIGN PATENT DOCUMENTS

| | | |
|---|---|---|
| EP | 2 404 932 A1 | 1/2012 |
| EP | 2 436 688 A1 | 4/2012 |
| JP | 2006-45214 | 2/2006 |
| JP | 2006-160640 | 6/2006 |
| JP | 2007-512842 | 5/2007 |
| WO | WO 01/12668 | 2/2001 |
| WO | WO 2005/049819 | 6/2005 |
| WO | WO 2005/090564 | 9/2005 |
| WO | WO 2006/054947 | 9/2006 |
| WO | WO 2008/096814 | 8/2008 |
| WO | WO 2008/096816 | 8/2008 |
| WO | WO 2010/101237 | 9/2010 |
| WO | WO 2010/137594 | 12/2010 |

OTHER PUBLICATIONS

Collado et al ('Vasoactive intestinal peptide enhances growth and angiogenesis of human experimental prostate cancer in a xenograft model' Peptides v28 2007 pp. 1896-1901).*
European Search Report for European patent application EP 10 78 0549 (which is a counterpart of copending U.S. Appl. No. 13/322,424) prepared Dec. 6, 2012 and mailed Dec. 18, 2012.
Nakagami, et al., "Modification of a novel angiogenic peptide, AG30, for the development of novel therapeutic agents," *J. Cell. Mol. Med.* 16(7):1629-1639 (Jun. 2012).
Nishikawa, et al., "Development of a novel antimicrobial peptide, AG-30, with angiogenic properties," *J. Cell. Mol. Med.* 13(3):535-546 (Mar. 2009).
Nishkawa, et al., "Analysis of *De Novo* Engineered Variants of AG-30 for the Treatment of Ischemic Diseases and Infectious Diseases," abstract from the 14th Annual Meeting of the Japan Society of Gene Therapy (Jun. 12-14, 2008), Abstract No. 37, published in *J. Gene Med.* 11:1138-1190, see pp. 1166-1167 (Dec. 2009).

(Continued)

Primary Examiner — Karlheinz R Skowronek
Assistant Examiner — Ronald Niebauer
(74) Attorney, Agent, or Firm — Leydig, Voit & Mayer, Ltd.

(57) ABSTRACT

Novel polypeptides which have an excellent angiogenesis-inducing activity and an excellent antibacterial activity and medical uses thereof are disclosed. The amino acid sequences of the novel polypeptides are shown in any one of SEQ ID NOs:1 to 6. These polypeptides have angiogenesis-inducing and antibacterial activities. Such polypeptides are useful for the prevention, amelioration or treatment of skin wounds caused by a cut wound, surgical wound, erosion, burn, decubitus, intractable wound, skin ulcer, leg ulcer, diabetic ulcer, occlusive arterial disease or arteriosclerosis obliteran, and for the prevention, amelioration or treatment of bacterial infection in such skin wounds, and the like.

29 Claims, 7 Drawing Sheets

(56) References Cited

OTHER PUBLICATIONS

International Search Report for PCT/JP2010/053618 filed Mar. 5, 2010, (counterpart of co-pending U.S. Appl. No. 13/254,843).
International Preliminary Report on Patentability for PCT/JP2010/053618 filed Mar. 5, 2010, (counterpart of co-pending U.S. Appl. No. 13/254,843).
Written Opinion of the International Searching Authority for PCT/JP2010/053618 filed Mar. 5, 2010, (counterpart of co-pending U.S. Appl. No. 13/254,843).
International Search Report for PCT/JP2010/058838 filed May 25, 2010, (counterpart of co-pending U.S. Appl. No. 13/322,424).
International Preliminary Report on Patentability for PCT/JP2010/058838 filed May 25, 2010, (counterpart of co-pending U.S. Appl. No. 13/322,424).
Written Opinion of the International Searching Authority for PCT/JP2010/058838 filed May 25, 2010, (counterpart of co-pending U.S. Appl. No. 13/322,424).
International Search Report for PCT/JP2009070035 filed Nov. 27, 2009.
International Preliminary Report on Patentability for PCT/JP2009070035 filed Nov. 27, 2009.
Written Opinion of the International Searching Authority for PCT/JP2009070035 filed Nov. 27, 2009.
Aurora, et al., "Helix capping," *Protein Science* 7(1):21-38 (1998).
Brenneman, et al., "Protective Peptides That are Orally Active and Mechanistically Nonchiral," *J. Pharmacol. Exp. Ther.* 309(3):1190-1197 (2004).
D'Andrea, et al., "Targeting angiogenesis: Structural characterization and biological properties of a de novo engineered VEGF mimicking peptide," *Proc. Natl. Acad. Sci. USA* 102(40):14215-14220 (Oct. 4, 2005).
Dharap, et al., "Tumor-specific targeting of an anticancer drug delivery system by LHRH peptide," *Proc. Natl. Acad. Sci. USA* 102(36):12962-12967 (Sep. 6, 2005).
Hayward, et al., "Fibroblast growth factor reverses the bacterial retardation of wound contraction," *Am. J. Surg.* 163(3):288-293 (Mar. 1992).
Herouy, et al., "Matrix metalloproteinases and venous leg ulceration," *Eur. J. Dermat.* 10(3):173-180 (2000).
Koczulla, et al., "An angiogenic role for the human peptide antibiotic LL-37/hCAP-18," *J. Clin. Invest.* 111(11):1665-1672 (Jun. 2003).
Martinez, et al., "Proadrenomedullin $NH_2$-Terminal 20 Peptide Is a Potent Angiogenic Factor, and Its Inhibition Results in Reduction of Tumor Growth," *Cancer Res.* 64(18):6489-6494 (Sep. 15, 2004).
Nakagami, et al., "Anti-microbial Peptide and angiogenesis," *J. Jpn. Coll. Angiol.* 48:437-440 (2008).
Sato, et al., "Glycoinsulins: Dendritic Sialyloligosaccharide-Displaying Insulins Showing a Prolonged Blood-Sugar-Lowering Activity," *J. Am. Chem. Soc.* 126(43):14013-14022 (2004).
Sato, et al., "Site-Specific Introduction of Sialic Acid into Insulin," *Angew. Chem. Int. Ed.* 43(12):1516-1520 (2004).
Shinoyama, et al., "Cutaneous Ulceration," *Japanese Journal of Clinical Dialysis* 24(7):819-821 (2008).
Sawai, et al., "Impact of single-residue mutations on the structure and function of ovispirin/novispirin antimicrobial peptides," *Protein Eng.* 15(3):225-232 (2002).
Stenberg, et al., "Effect of bFGH on the inhibition of contraction caused by bacteria," *J. Surg. Res.* 50(1):47-50 (1991).
Ulbricht, et al., "The Use of PEG-Hirudin in chronic hemo-dialysis monitored by the Ecarin Clotting Time: influence on clotting of the extracorporeal system and hemostatic parameters," *Clin. Nephrol.* 65(3):180-190 (2006).
Wilkemeyer, et al., "Ethanol Antagonist Peptides: Structural Specificity without Stereospecificity," *J. Pharmacol. Exp. Ther.* 309(3):1183-1189 (2004).
Zanetti, et al., "Cathelicidins multifunctional peptides of the innate immunity," *J. Leukoc. Biol.* 75(7):39-48 (Jan. 2004).
Zasloff, et al., "Magainins, a class of antimicrobial peptides from *Xenopus* skin: Isolation, characterization of two active forms, and partial cDNA sequence of a precursor," *Proc. Natl. Acad. Sci. USA* 84(15):5449-5453 (Aug. 1987).
English translation of Siiinoyama, et al., "Cutaneous Ulceration," *Japanese Journal of Clinical Dialysis* 24(7):819-821 (2008).
Machine translation of WO 2008/096814 (document B7 in IDS filed on Nov. 10, 2012); Nakagami, et al., published Aug. 14, 2008.
Machine translation of WO 2008/096816 (document B8 in IDS filed on Nov. 10, 2012); Nakagami, et al., published Aug. 14, 2008.
Strömstedt, et al., "Evaluation of Strategies for Improving Proteolytic Resistance of Antimicrobial Peptides by Using Variants of EFK17, an Internal Segment of LL-37," *Antimicrobial Agents and Chemotherapy* 53:593-602 (Feb. 2009).
Office Action for copending U.S. Appl. No. 13/322,424, sent Nov. 20, 2013.
Response to Restriction Requirement for copending U.S. Appl. No. 13/322,424, filed Aug. 29, 2013.
Restriction Requirement for copending U.S. Appl. No. 13/322,424, sent Jul. 30, 2013.
Response to Office Action for copending U.S. Appl. No. 13/322,424, filed by Applicants on Mar. 13, 2014.
Applicant-submitted Translation of paragraphs 18 and 21 of WO 2008/096816, published on Aug. 14, 2008.
Extended European Search Report for EP 09829160.2, prepared May 3, 2012.
English Language Abstract for WO 2008/096814, published on Aug. 14, 2008.
English Language Abstract for WO 2008/096816, published on Aug. 14, 2008.
López-Garcia, et al., "Anti-Fungal Activity of Cathelicidins and their Potential Role in *Candida albicans* Skin Infection," *J. Invest. Dermatol.* 125(1):108-115 9 (Jul. 2005).
Uniprot Database Accession No. C0PK96, entered May 5, 2009.
Response to Office Action of Jun. 25, 2014, filed with RCE for copending U.S. Appl. No. 13/322,424 on Sep. 25, 2014.
Terminal Disclaimer filed with Response to Office Action of Jun. 25, 2014 for copending U.S. Appl. No. 13/322,424 (document C1 herein). The terminal disclaimer was submitted on Sep. 25, 2014.
Office Action for copending U.S. Appl. No. 13/322,424, sent Jun. 25, 2014.
Matsuzaki, et al., "Control of cell selectivity of antimicrobial peptides," *Biochim. Biophys. Acta* 1788:1687-1692 (first available online Oct. 8, 2008).
Notice of Allowance for copending U.S. Appl. No. 13/322,424, mailed Oct. 24, 2014.

\* cited by examiner

```
SEQUENCE LISTING

<160> NUMBER OF SEQ ID NOS: 7

<210> SEQ ID NO 1
<211> LENGTH: 20
<212> TYPE: PRT
<213> ORGANISM: Artificial Sequence
<220> FEATURE:
<223> OTHER INFORMATION: SR-1. Chemically synthesized peptide.

<400> SEQUENCE: 1

Met Leu Lys Leu Ile Phe Leu His Arg Leu Lys Arg Met Arg Lys Arg
1               5                   10                  15

Leu Lys Arg Lys
            20

<210> SEQ ID NO 2
<211> LENGTH: 21
<212> TYPE: PRT
<213> ORGANISM: Artificial Sequence
<220> FEATURE:
<223> OTHER INFORMATION: SR-2. Chemically synthesized peptide.
<220> FEATURE:
<221> NAME/KEY: MOD_RES
<222> LOCATION: (21)..(21)
<223> OTHER INFORMATION: The C-terminal arginine residue is modified by
      amidation.

<400> SEQUENCE: 2

Glu Leu Arg Phe Leu His Arg Leu Lys Arg Arg Leu Arg Lys Arg Leu
1               5                   10                  15

Lys Arg Lys Leu Arg
```

20

<210> SEQ ID NO 3
<211> LENGTH: 20
<212> TYPE: PRT
<213> ORGANISM: Artificial Sequence
<220> FEATURE:
<223> OTHER INFORMATION: SR-3. Chemically synthesized peptide.
<220> FEATURE:
<221> NAME/KEY: MOD_RES
<222> LOCATION: (20)..(20)
<223> OTHER INFORMATION: The C-terminal arginine residue is modified by
      amidation.

<400> SEQUENCE: 3

Glu Leu Arg Phe Leu His Arg Leu Lys Arg Met Arg Lys Arg Leu Lys
1               5                   10                  15

Arg Lys Leu Arg
            20

<210> SEQ ID NO 4
<211> LENGTH: 20
<212> TYPE: PRT
<213> ORGANISM: Artificial Sequence
<220> FEATURE:
<223> OTHER INFORMATION: SR-4. Chemically synthesized peptide.
<220> FEATURE:
<221> NAME/KEY: MOD_RES
<222> LOCATION: (20)..(20)
<223> OTHER INFORMATION: The C-terminal arginine residue is modified by
      amidation.

<400> SEQUENCE: 4

Lys Leu Ile Phe Leu His Arg Leu Lys Arg Met Arg Lys Arg Leu Lys
1               5                   10                  15

Arg Lys Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: SR-5. Chemically synthesized peptide.

<400> SEQUENCE: 5

Lys Arg Met Arg Lys Arg Leu Lys Arg Lys Leu Arg Leu Trp His Arg
1               5                   10                  15

Lys Arg Tyr Lys
            20

<210> SEQ ID NO 6
<211> LENGTH: 18
<212> TYPE: PRT
<213> ORGANISM: Artificial Sequence
<220> FEATURE:
<223> OTHER INFORMATION: SR-6. Chemically synthesized peptide.
<220> FEATURE:
<221> NAME/KEY: MOD_RES
<222> LOCATION: (18)..(18)
<223> OTHER INFORMATION: The C-terminal lysine residue is modified by
      amidation.

<400> SEQUENCE: 6

Met Arg Lys Arg Leu Lys Arg Lys Leu Arg Leu Trp His Arg Lys Arg
1               5                   10                  15

Tyr Lys

```
<210> SEQ ID NO 7
<211> LENGTH: 30
<212> TYPE: PRT
<213> ORGANISM: Artificial Sequence
<220> FEATURE:
<223> OTHER INFORMATION: AG30-5C. Chemically synthesized peptide.

<400> SEQUENCE: 7

Met Leu Lys Leu Ile Phe Leu His Arg Leu Lys Arg Met Arg Lys Arg
1               5                   10                  15

Leu Lys Arg Lys Leu Arg Phe Trp His Arg Lys Arg Tyr Lys
            20                  25                  30
```

POLYPEPTIDE HAVING ANGIOGENESIS-INDUCING ACTIVITY AND ANTIBACTERIAL ACTIVITY, AND USE THEREOF FOR MEDICAL PURPOSES

CROSS REFERENCE TO RELATED APPLICATIONS

The present application is US national stage of international application, PCT/JP2009/070035 which had an international filing date of Nov. 27, 2009, and which was published in Japanese under PCT Article 21(2) on Jun. 3, 2010. Priority is claimed to Japanese application JP 2008-303502, filed on Nov. 28, 2008.

TECHNICAL FIELD

The present invention relates to novel polypeptides which have an angiogenesis-inducing activity and an antibacterial activity, an angiogenesis-inducing agent containing the polypeptide, an agent for treating a skin wound(s) containing the polypeptide, and an agent for preventing skin wound infection containing the polypeptide.

BACKGROUND ART

In the treatment of various diseases or injuries including burns, decubituses, wounds, skin ulcers, leg ulcers, diabetic ulcers, occlusive arterial disease and arteriosclerosis obliterans, angiogenesis is useful. Since serious exacerbation of the pathological condition may be induced by bacterial infection in these diseases, an angiogenesis-inducing agent which has both an antibacterial activity and an angiogenesis-inducing activity is demanded.

Also, in skin wounds associated with bacterial infection, an agent for treating a wound(s) which has an antibacterial activity is useful. Moreover, in view of preventing possible future infection, it is desired that an agent for treating a wound(s) having an antibacterial activity be also used for wounds which are not associated with infection.

As a polypeptide which has an angiogenesis-inducing activity and an antibacterial activity, LL-37 is known (Non Patent Literatures 1 and 2).

Besides, Nakagami et al. invented a polypeptide which has a vascular endothelial growth activity, and in turn, an angiogenesis-inducing activity, and further discovered that the peptide has a peptide having a higher angiogenesis-inducing activity than LL-37, and then filed a patent application directed thereto (Patent Literature 1). Furthermore, Nakagami et al. discovered a polypeptide AG30-5C, which consists of 30 amino acid residues and has a higher angiogenesis-inducing activity than the peptide of Patent Literature 1, and then filed a patent application directed thereto (Patent Literature 2). Patent Literature 1 and 2 also suggest that the polypeptides have an antibacterial activity.

In addition, as a therapeutic agent for decubitus or skin ulcer, a formulation which contains basic FGF (bFGF) consisting of 154 amino acids as an effective ingredient (FIBLAST Spray (registered trademark)) is known. However, this bFGF does not have an antibacterial activity.

PRIOR ART REFERENCES

Patent Literatures

Patent Literature 1 WO 2005/090564 A1
Patent Literature 2 WO 2008/096816 A1

Non Patent Literatures

Non-patent Literature 1 Koczulla R, von Degenfeld G, Kupatt C, Krotz F, Zahler S, Gloe T, Issbrucker K, Unterberger P, Zaiou M, Lebherz C, Karl A, Raake P, Pfosser A, Boekstegers P, Welsch U, Hiemstra P S, Vogelmeier C, Gallo R L, Clauss M, Bals R., "An angiogenic role for the human peptide antibiotic LL-37/hCAP-18.", J Clin Invest. 2003 June; 111(11):1665-72
Non-patent Literature 2 Zanetti M., "Cathelicidins, multifunctional peptides of the innate immunity.", J Leukoc Biol. 2004 January; 75(1):39-48. Epub 2003 July 22.

DISCLOSURE OF THE INVENTION

Problems to be Solved by the Invention

An object of the present invention is to provide novel polypeptides which have a higher angiogenesis-inducing activity and a more antibacterial activity than known polypeptides, a novel angiogenesis-inducing agent which contains the polypeptide as an effective ingredient, a novel agent for treating a skin wound(s) including a skin ulcer or an intractable wound which contains the polypeptide as an effective ingredient, and a novel agent for treating a skin wound(s) associated with infection which contains the polypeptide as an effective ingredient.

Means for Solving the Problems

The present inventors intensively studied to discover polypeptides which have a higher angiogenesis-inducing activity and a higher antibacterial activity than the polypeptides described in Patent Literature 1 and 2, thereby completing the present invention.

That is, the present invention provides:
(1) A polypeptide whose amino acid sequence is shown in any one of SEQ ID NOs:1 to 6.
(2) An angiogenesis-inducing agent comprising the polypeptide according to (1) as an effective ingredient.
(3) The angiogenesis-inducing agent according to (2), wherein the amino acid sequence of said polypeptide is shown in SEQ ID NO:1, 2 or 3.
(4) An antibacterial agent, comprising the polypeptide according to (1) as an effective ingredient.
(5) A method for inducing angiogenesis, said method comprising administering an effective amount of the polypeptide according to (1) to a mammal in need of angiogenesis.
(6) Use of the polypeptide according to (1) for the production of an angiogenesis-inducing agent.
(7) A polypeptide for inducing angiogenesis, which is the polypeptide according to (1).
(8) An agent for the prevention, amelioration or treatment of a skin wound(s), said agent comprising the polypeptide according to (1) as an effective ingredient.
(9) The agent for the prevention, amelioration or treatment of a skin wound(s) according to (8), wherein the skin wound(s) is(are) selected from the group consisting of skin wounds caused by cut wounds, surgical wounds, erosions, burns, decubituses, intractable wounds, skin ulcers, leg ulcers, diabetic ulcers, occlusive arterial disease and arteriosclerosis obliterans.
(10) The agent for the prevention, amelioration or treatment according to (9), wherein the skin wound is an intractable wound.

(11) The agent for the prevention, amelioration or treatment according to (9), wherein the skin wound is a wound associated with infection.

(12) An agent for the prevention, amelioration or treatment of bacterial infection in a skin wound(s), comprising the polypeptide according to (1) as an effective ingredient.

(13) A method for the prevention, amelioration or treatment of a skin wound(s) or bacterial infection in a skin wound(s), which comprises administering an effective amount of the polypeptide according to (1) to a mammal.

(14) Use of the polypeptide according to (1) for producing an agent for the prevention, amelioration or treatment of a skin wound(s) or bacterial infection in a skin wound(s).

(15) A polypeptide for the prevention, amelioration or treatment of a skin wound(s) or bacterial infection in a skin wound(s), which is the polypeptide according to (1).

Effects of Invention

The present invention provided novel polypeptides which have an excellent angiogenesis-inducing activity and an excellent antibacterial activity. The present invention also provided a novel angiogenesis-inducing agent which contains the polypeptide as effective ingredient, a novel agent for treating a skin wound(s) including cut wounds, surgical wounds, erosions, various skin ulcers, intractable wounds which contains the polypeptide as effective ingredient, and a novel agent for treating a skin wound(s) associated with infection which contains the polypeptide as effective ingredient. Since the agents for treating a wound(s) of the present invention have both of a activity to prevent and/or treat infection and a activity to promote wound tissue regeneration, they are excellent as a therapeutic agent of an agent for treating a skin wound(s).

MODE FOR CARRYING OUT INVENTION

Figure 1:
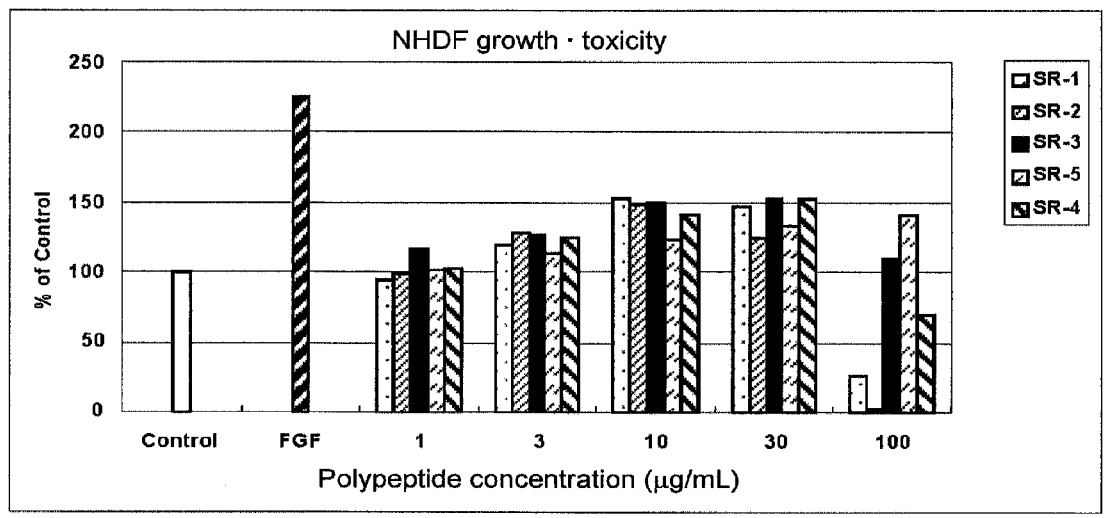
FIG. 1 shows the results obtained by examining the effect of the polypeptides of the present invention on the growth of human dermal fibroblasts (NHDF). The values are relative values obtained by taking the measured value of a negative control (Control) group as 100.
Figure 2A:
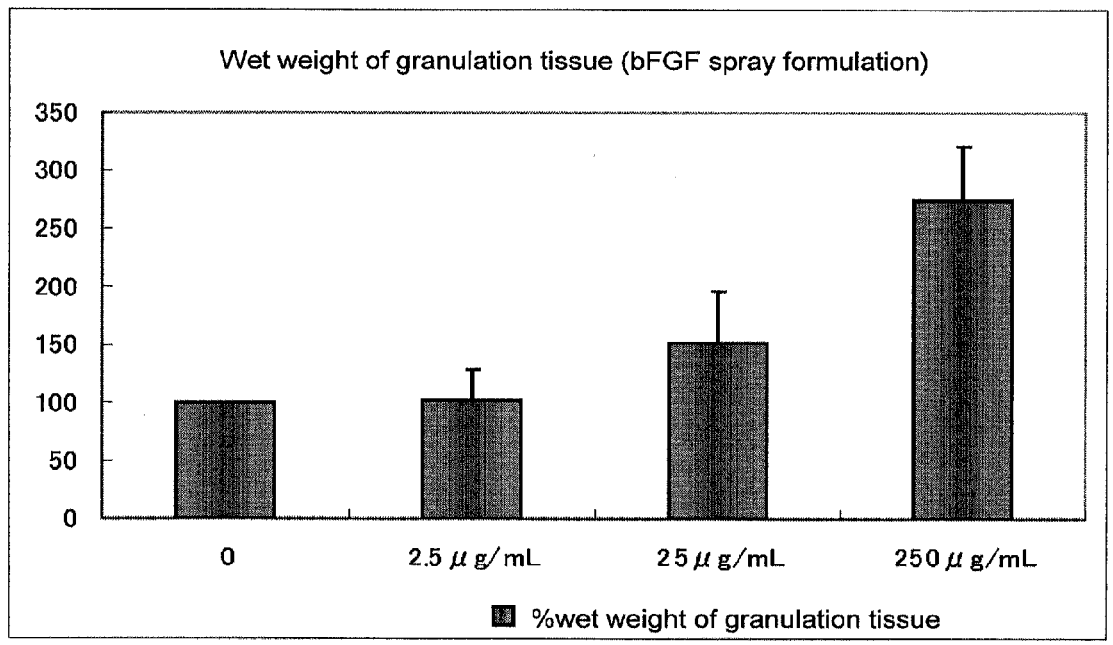
FIG. 2A shows the results obtained by measuring the ability to form granulation tissue in paper disc model impregnated with the bFGF formulation as a positive control. The terms 2.5 μg/mL, 25 μg/mL and 250 μg/mL mean the dosages of 0.1 μg/disc, 1.0 μg/disc and 10 μg/disc, respectively.
Figure 2B:
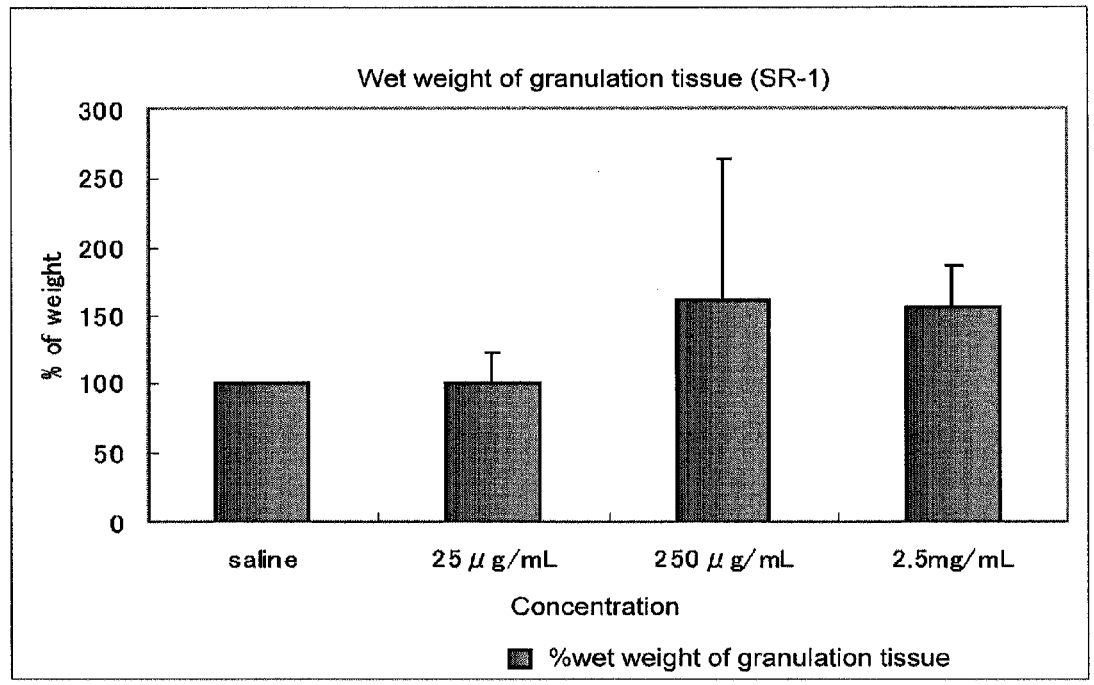
FIG. 2B shows the results obtained by measuring the ability to form granulation tissue in paper disc model impregnated with SR-1, one of the polypeptides of the present invention. The terms 25 μg/mL, 250 μg/mL and 2.5 mg/mL mean the dosages of 1.0 μg/disc, 10 μg/disc and 100 μg/disc, respectively.
Figure 2C:
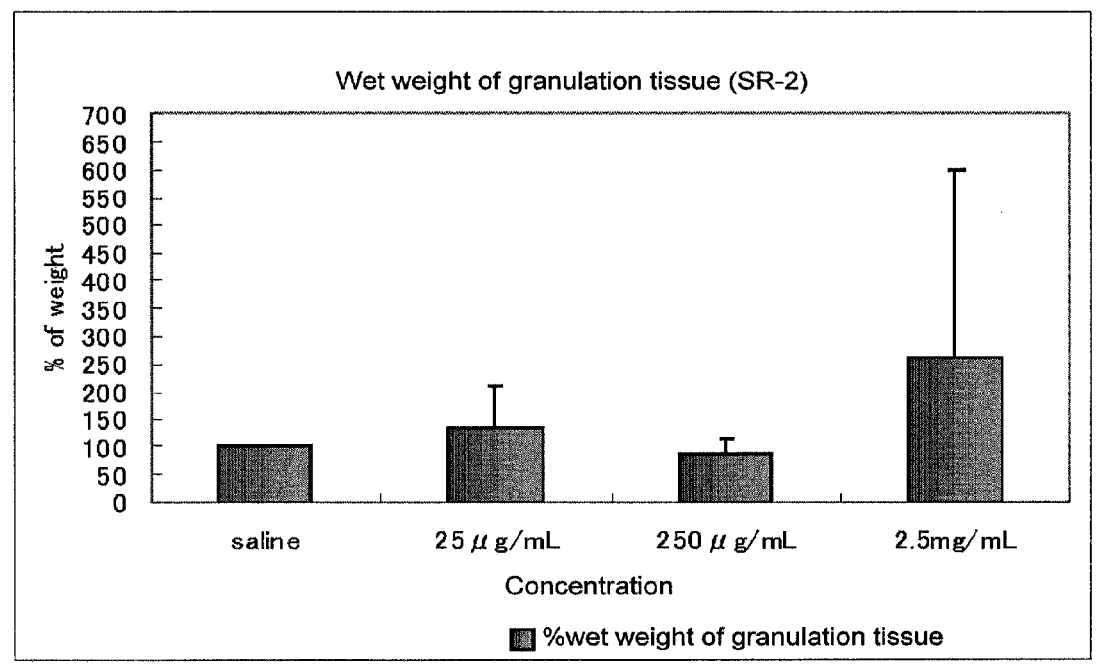
FIG. 2C shows the results obtained by measuring the ability to form granulation tissue in paper disc model impregnated with SR-2, one of the polypeptides of the present invention. The terms 25 μg/mL, 250 μg/mL and 2.5 mg/mL mean the dosages of 1.0 μg/disc, 10 μg/disc and 100 μg/disc, respectively.
Figure 2D:
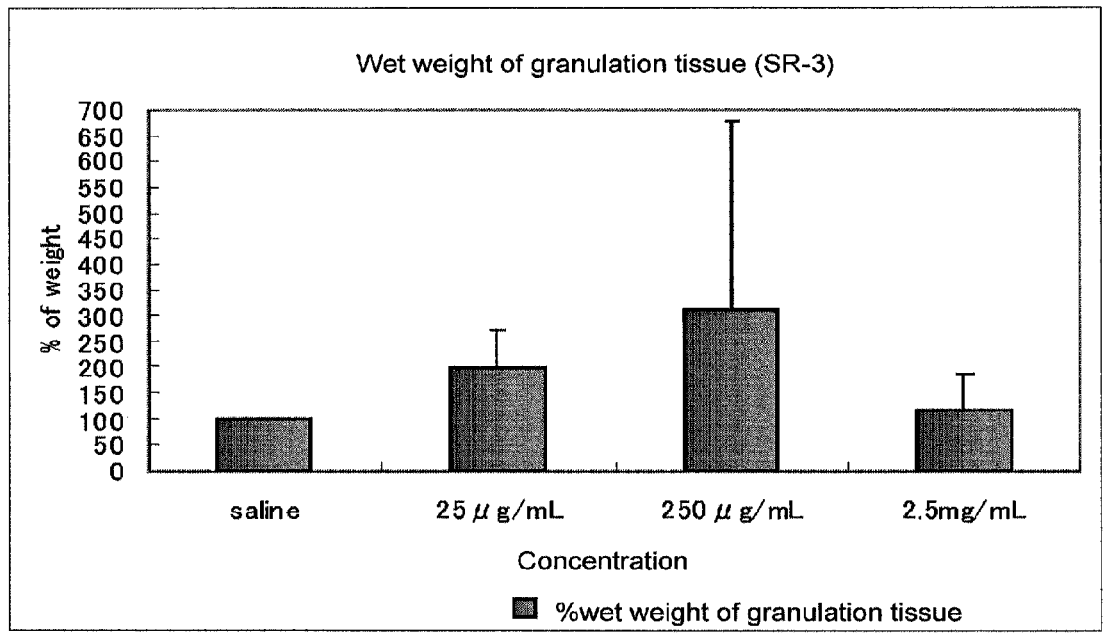
FIG. 2D shows the results obtained by measuring the ability to form granulation tissue in paper disc model impregnated with SR-3, one of the polypeptides of the present invention. The terms 25 μg/mL, 250 μg/mL and 2.5 mg/mL mean the dosages of 1.0 μg/disc, 10 μg/disc and 100 μg/disc, respectively.
Figure 2E:
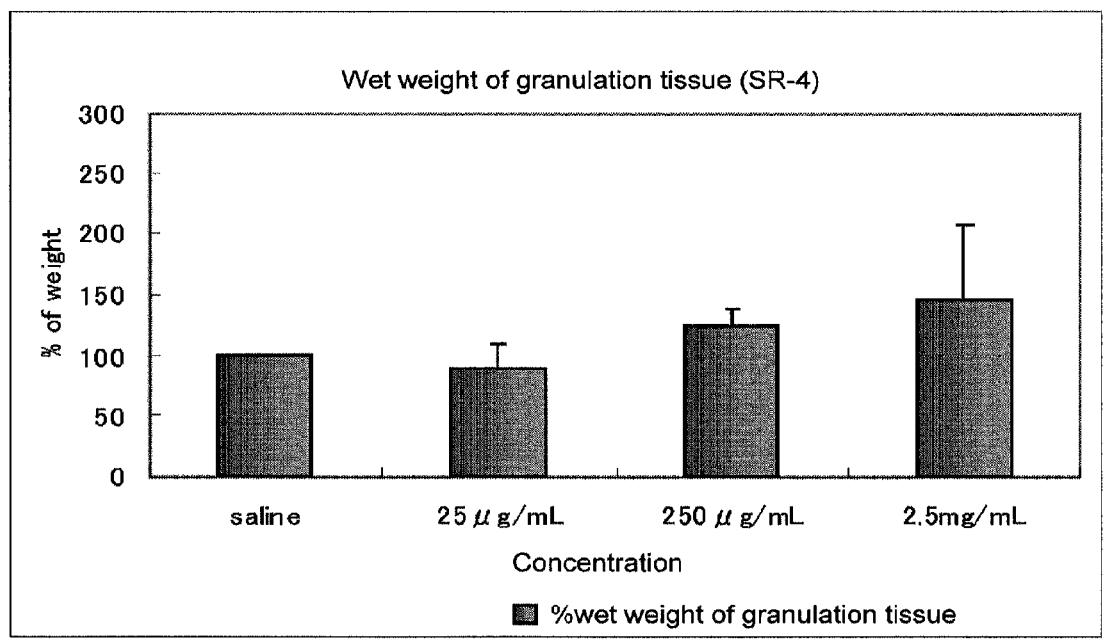
FIG. 2E shows the results obtained by measuring the ability to form granulation tissue in paper disc model impregnated with SR-4, one of the polypeptides of the present invention. The terms 25 μg/mL, 250 μg/mL and 2.5 mg/mL mean the dosages of 1.0 μg/disc, 10 μg/disc and 100 μg/disc, respectively.
Figure 2F:
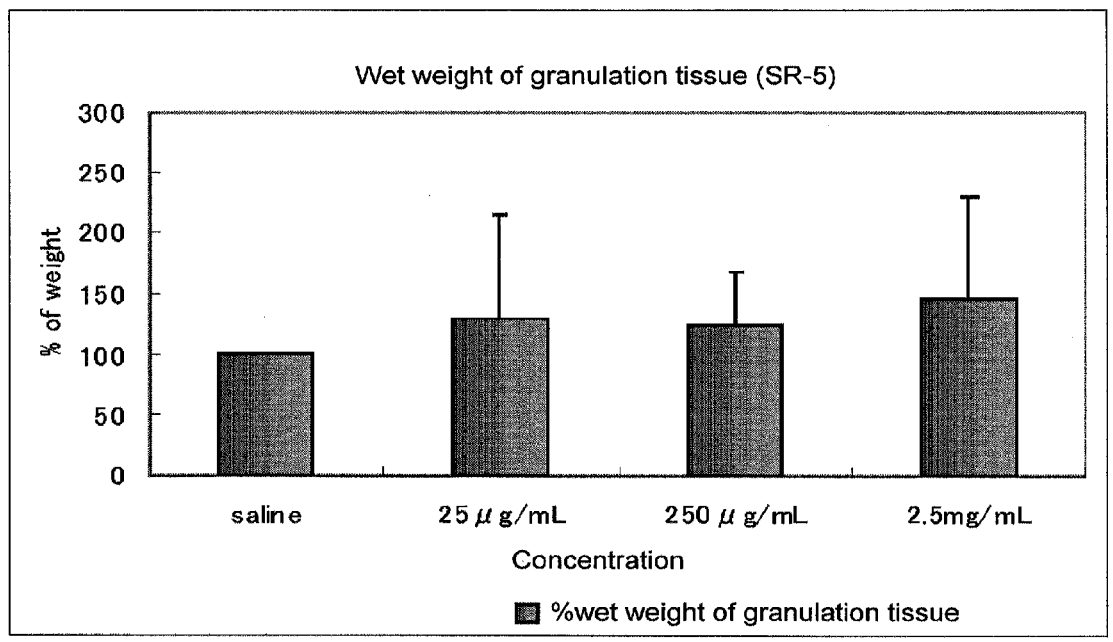
FIG. 2F shows the results obtained by measuring the ability to form granulation tissue in paper disc model impregnated with SR-5, one of the polypeptides of the present invention. The terms 25 μg/mL, 250 μg/mL and 2.5 mg/mL mean the dosages of 1.0 μg/disc, 10 μg/disc and 100 μg/disc, respectively.
Figure 3A:
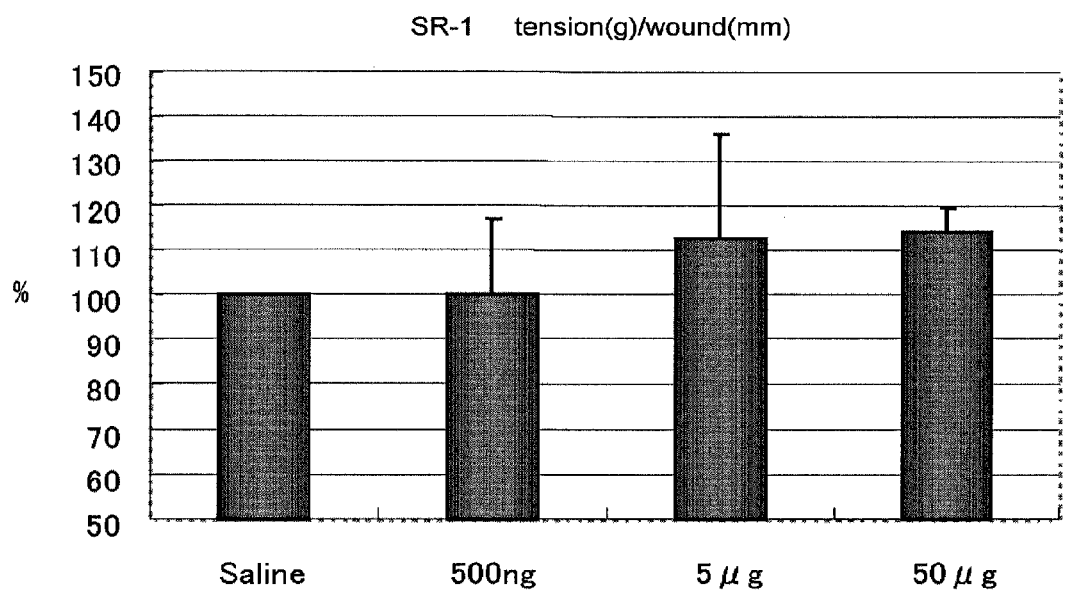
FIG. 3A shows the results obtained by administering SR-1, one of the polypeptides of the present invention, to a cut wound, and then measuring the wound closing tension of the cut wound.
Figure 3B:
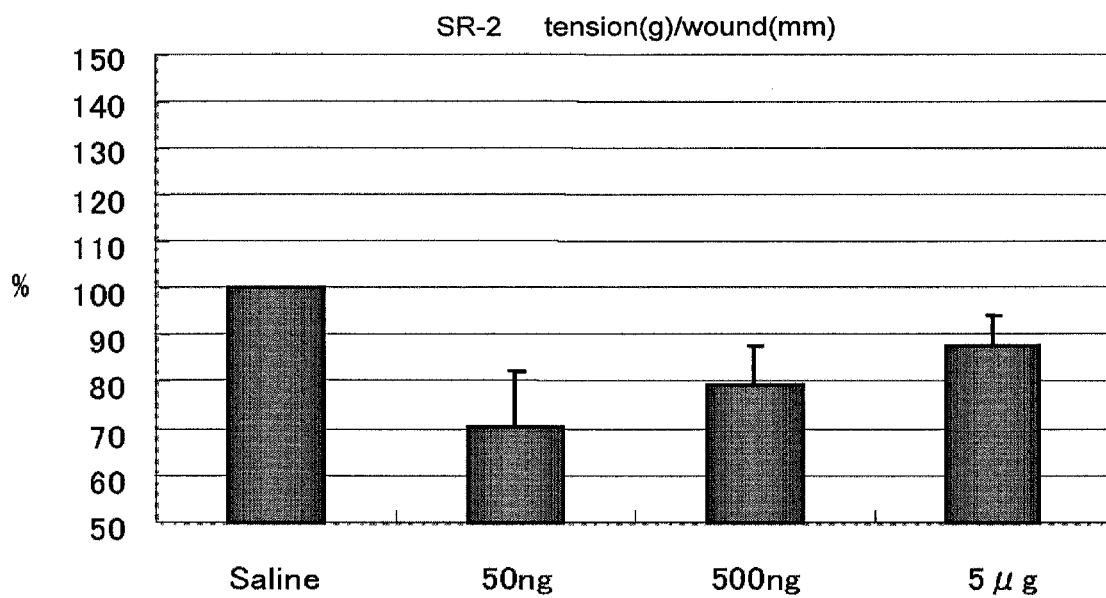
FIG. 3B shows the results obtained by administering SR-2, one of the polypeptides of the present invention, to a cut wound, and then measuring the wound closing tension of the cut wound.
Figure 3C:
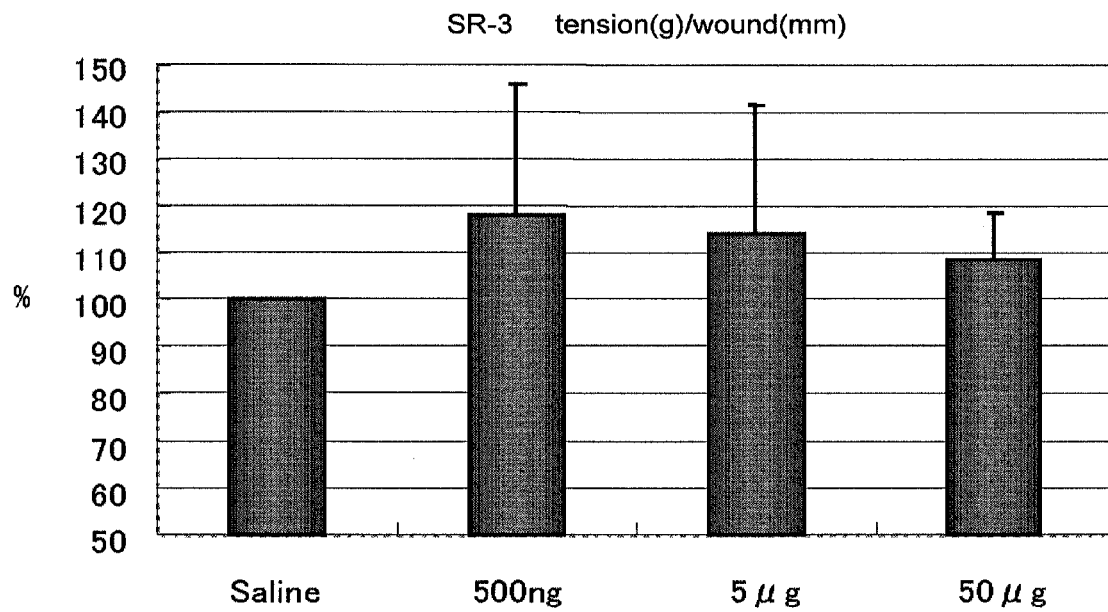
FIG. 3C shows the results obtained by administering SR-3, one of the polypeptides of the present invention, to a cut wound, and then measuring the wound closing tension of the cut wound.
Figure 3D:
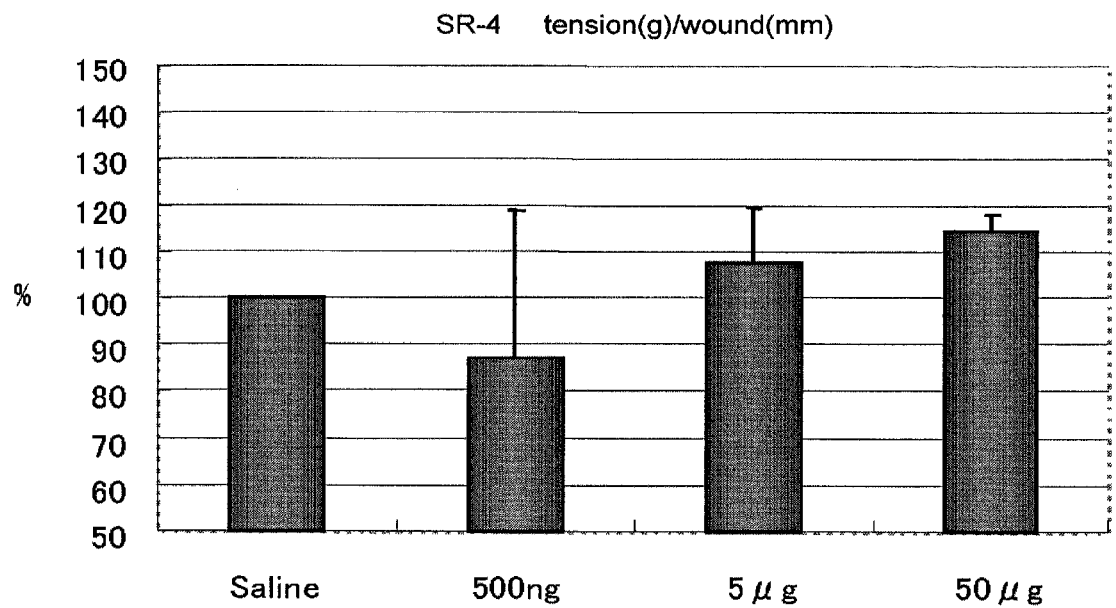
FIG. 3D shows the results obtained by administering SR-4, one of the polypeptides of the present invention, to a cut wound, and then measuring the wound closing tension of the cut wound.
Figure 3E:
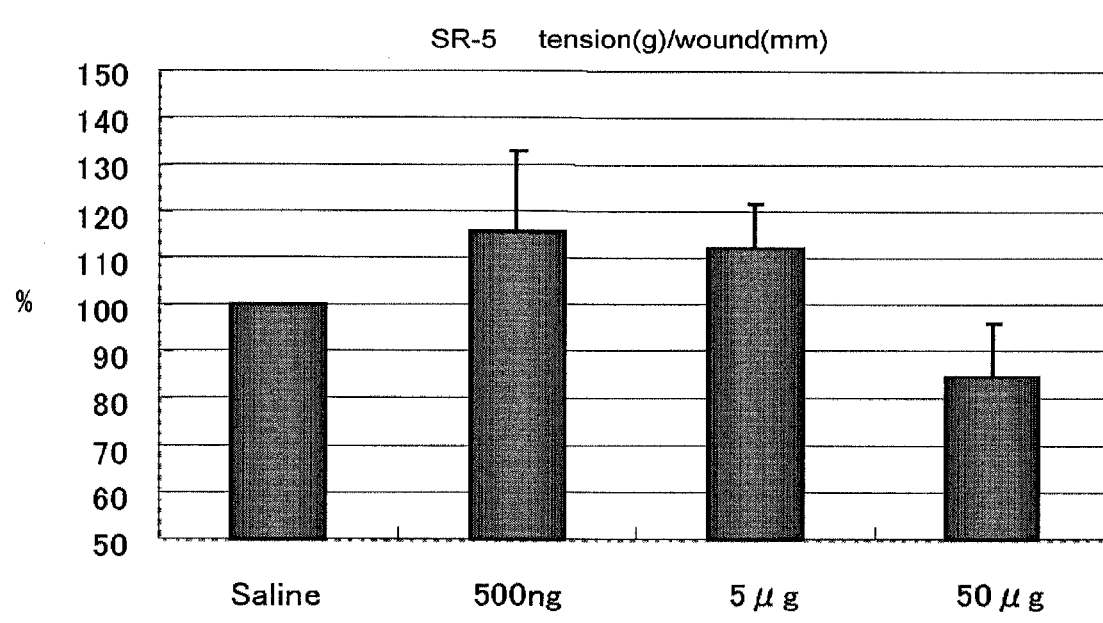
FIG. 3E shows the results obtained by administering SR-5, one of the polypeptides of the present invention, to a cut wound, and then measuring the wound closing tension of the cut wound.
Figure 3F:
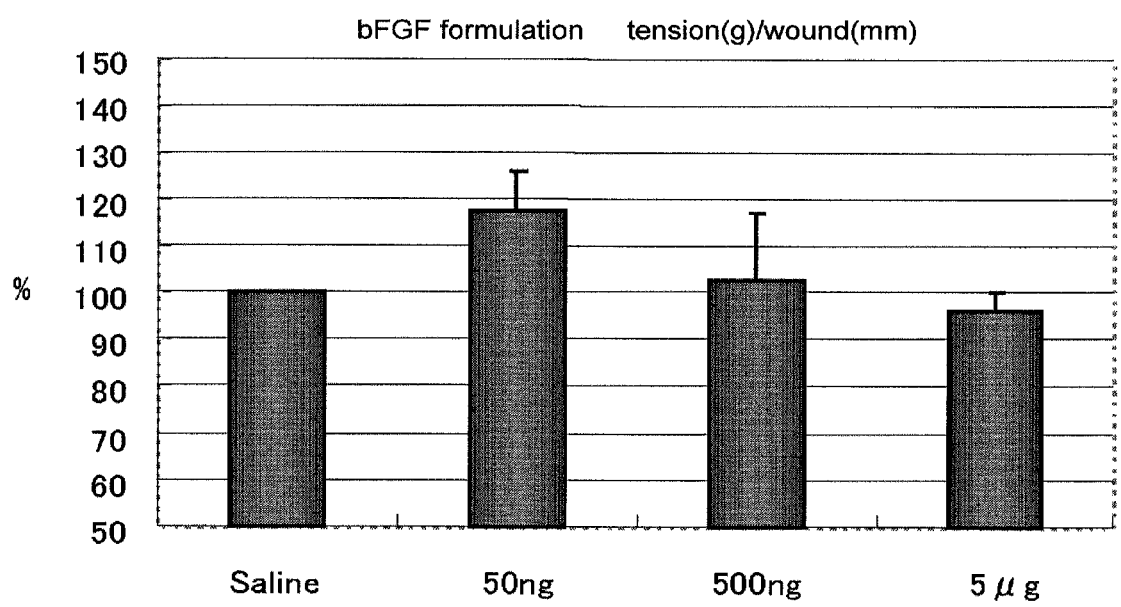
FIG. 3F shows the results obtained by administering the bFGF formulation, a control, to a cut wound, and then measuring the wound closing tension of the cut wound.

As described above, the amino acid sequences of the polypeptides of the present invention are shown in each of SEQ ID NOs:1 to 6. All of these polypeptides are novel substances.

The amino acid sequence of AG30-5C, which is the polypeptide described in Patent Literature 2, is shown in SEQ ID NO:7. As concretely described in Patent Literature 2 and the Examples below, AG30-5C has an antibacterial activity and an angiogenesis-inducing activity. It was proved that the above-described polypeptides of the present invention have an angiogenesis-inducing activity and an antibacterial activity. And, as concretely described in the Examples below, the polypeptides which are the examples of the present invention have a higher angiogenesis-inducing activity and a higher antibacterial activity than AG30-5C.

In general, with respect to a pharmaceutical composed of a polypeptide(s), techniques to increase the stability of the polypeptide(s) in vivo, wherein a sugar chain(s) and/or a polyethylene glycol (PEG) chain(s) is(are) added to the polypeptide(s), or wherein a D-amino acid(s) is(are) used as at least one part of the amino acids constituting the polypeptide(s), are widely known and used. The addition of a sugar chain(s) and/or a PEG chain(s) to a polypeptide, or the use of a D-amino acid(s) as at least one part of the amino acids constituting a polypeptide makes the polypeptide more unlikely to be decomposed by a peptidase(s) in vivo, and in turn, makes the half-life of the polypeptide in vivo longer. It is also well-known that acetylation of the N-terminus and/or amidation of the C-terminus of a peptide increases the stability of the peptide. The polypeptides of the present invention may be polypeptides which are modified with these known modifications for the stabilization in vivo, as long as they have an antibacterial activity. And, the term "polypeptide" as used herein and in the appended claims includes polypeptides which are modified with a modification(s) for the stabilization in vivo, unless the context clearly dictates otherwise. When the polypeptides of the present invention are such polypeptides which are modified with modifications for the stabilization, the amino acid sequence of their polypeptide moiety is shown in any one of SEQ ID NOs:1 to 6 as described above (wherein the amino acid which is acetylated or amidated as mention above is considered as the same amino acid as an amino acid which is not acetylated or amidated). Accordingly, the polypeptides which are modified with modifications for the stabilization include a polypeptide having an amino acid sequence shown in any one of SEQ ID NOs:1 to 6, to which a PEG-like structure(s) for the stabilization is(are) added, or wherein at least one part of its amino acids is changed into D-isomer, or whose N-terminus is acetylated and/or whose C-terminus is amidated, or which is modified with the combination of these modifications.

The addition of a sugar chain to a polypeptide is well-known, and described, for example, in Sato M, Furuike T, Sadamoto R, Fujitani N, Nakahara T, Niikura K, Monde K, Kondo H, Nishimura S., "Glycoinsulins: dendritic sialyloligosaccharide-displaying insulins showing a prolonged blood-sugar-lowering activity.", J Am Chem. Soc. 2004 Nov. 3; 126(43):14013-22, and Sato M, Sadamoto R, Niikura K, Monde K, Kondo H, Nishimura S, "Site-specific introduction of sialic acid into insulin.", Angew Chem Int Ed Engl. 2004 Mar. 12; 43(12):1516-20. A sugar chain can be bound to N-terminus, C-terminus or the amino acid therebetween, but it is preferred that a sugar chain be bound to N-terminus or C-terminus, in order not to inhibit the activity of the polypeptide. And, the number of the sugar chains is preferably one or two, more preferably one. The sugar chain is preferably from mono- to tetra-saccharide, more preferably disaccharide or trisaccharide. The sugar chain(s) can be bound directly to a free amino group(s) or a carboxyl group(s) on the polypeptide, or through a spacer structure(s) such as a methylene chain whose number of carbon atoms is about 1 to 10.

The addition of a PEG chain to a polypeptide is also well-known, and described, for example, in Ulbricht K, Bucha E, Poschel K A, Stein G, Wolf G, Nowak G., "The use of PEG-Hirudin in chronic hemodialysis monitored by the Ecarin Clotting Time: influence on clotting of the extracorporeal system and hemostatic parameters.", Clin Nephrol. 2006 March; 65(3):180-90, and Dharap S S, Wang Y, Chandna P, Khandare J J, Qiu B, Gunaseelan S, Sinko P J, Stein S, Farmanfarmaian A, Minko T., "Tumor-specific targeting of an anticancer drug delivery system by LHRH peptide.", Proc Natl Acad Sci USA. 2005 Sep. 6; 102(36):12962-7. A PEG chain can be bound to N-terminus, C-terminus or the amino acid therebetween, and one or two PEG chains are usually bound to a free amino group(s) and/or carboxyl group(s) on the polypeptide. The molecular weight of the PEG chain is not particularly limited, but typically about 3000 to 7000, preferably about 5000.

The method for changing at least one part of the amino acids constituting the polypeptide into D-isomer is also well-known, and described, for example, in Brenneman D E, Spong C Y, Hauser J M, Abebe D, Pinhasov A, Golian T, Gozes I., "Protective peptides that are orally active and mechanistically nonchiral.", J Pharmacol Exp Ther. 2004 June; 309(3):1190-7, and Wilkemeyer M F, Chen S Y, Menkari C E, Sulik K K, Charness M E., "Ethanol antagonist peptides: structural specificity without stereospecificity.", J Pharmacol Exp Ther. 2004 June; 309(3):1183-9. At least one part of the amino acids constituting the polypeptide may be a D-amino acid(s), but it is preferred that all of the amino acids constituting the polypeptide be D-amino acids, in order to inhibit the activity of the polypeptide as little as possible.

The polypeptides which are the effective ingredients of the angiogenesis-inducing agents of the present invention can be easily produced by conventional methods such as a chemical synthesis method using a commercially available peptide synthesizer. In addition, the above-described modifications for the stabilization can be also easily carried out by well-known methods as described in each of the above-mentioned documents.

Since the polypeptides of the present invention have a high angiogenesis-inducing activity, they can be used as an angiogenesis-inducing agent, and also can be used as an agent for treating a skin wound(s).

In the present description, the term "angiogenesis-inducing agent" refers to an agent which can induce and/or increase the angiogenesis in the site where the agent has been administered and in the vicinity thereof in cases where the agent has been topically administered to a living body. The induction of the angiogenesis can be evaluated by a known method such as measuring blood flow at such site. When the agent is topically administered to a wound site, the agent induces and/or increase the angiogenesis to promote granulation and skin tissue regeneration and thereby to promote healing.

In the present description, the term "antibacterial agent" refers to an agent which has an effect to kill bacteria which have already infected or suppress or reduce their growth, or an effect to suppress and/or inhibit infection by bacteria, in the case where the agent has been administered to a living body.

In the present description, the term "agent for treating a skin wound(s)" refers to an agent which provides promotion of healing or amelioration of the wound(s), or prevention or delay of the deterioration of the wound(s), in the case where the agent has been topically administered to the wound site and/or to the vicinity thereof. The promotion of the healing or amelioration of a wound(s) refers to promotion of early reduction of an area of a wound site, or promotion of granulation and/or skin tissue regeneration at a wound site.

How to use the angiogenesis-inducing agents and the agents for treating a skin wound(s), and the below-described agents for the prevention, amelioration or treatment of a skin wound(s), and the below-described methods of using them as an agent for the prevention, amelioration or treatment of bacterial infection in a skin wound(s), is the same as known polypeptide-based angiogenesis-inducing agents. They can be administered as solutions, emulsions, suspensions, dusts, powders, granules, gels, ointments, or transdermal patches, especially preferably as solutions, dusts, or transdermal patches. Preferably, a buffer solution, especially preferably a solution dissolved in an aqueous medium such as a physiological saline buffer solution, can be administered as the solution. The concentration of the polypeptide in the solution is not particularly limited, but usually about 0.01 mg/mL to 100 mg/mL, preferably about 0.1 mg/mL to 50 mg/mL, especially preferably about 1 mg/mL to 10 mg/mL. In general, the administration route is a topical administration such as spraying, applying and injecting to a site(s) which require(s) angiogenesis, or healing or amelioration of a wound(s). The dosage may be appropriately selected depending on the symptom, the size of the affected part, or the like. In general, the dosage is, in terms of the polypeptide, about 0.01 mg to 100 mg, preferably about 0.005 mg to 50 mg, especially preferably about 0.005 mg to 0.5 mg, but not limited to these ranges, of course. For example, the single dose can be about 0.05 mg.

Alternatively, the dosage can also be set depending on the area of a site which requires angiogenesis, or healing or amelioration of a wound(s). For example, the dosage can be 1 to 100 µg/cm².

As a pharmaceutically acceptable carrier which is used in formulating the angiogenesis-inducing agent of the present invention, in addition to the aqueous medium as mentioned above, carriers which are commonly used in the field of pharmaceutical formulation can be used. For example, in the case of an external preparation such as an ointment, the pharmaceutically acceptable carriers include hydrocarbons (hydrophilic petrolatum, white petrolatum, purified lanolin, liquid paraffin, etc.), zinc oxide, higher fatty acids and the esters thereof (adipic acid, myristic acid, palmitic acid, stearic acid, oleic acid, adipic acid ester, myristic acid ester, palmitic acid ester, diethyl sebacate, hexyl laurate, cetyl isooctanoate, etc.), waxes (spermaceti, beeswax, ceresin, etc.), and higher alcohols (cetanol, stearyl alcohol, cetostearyl alcohol, etc.). In the case of a solution, the pharmaceutically acceptable carriers include water, physiological saline, and phosphate-buffered physiological saline, for example. In the case of an oral preparation, the pharmaceutically acceptable carriers include lactose and starch, for example. In addition to these, as necessary, various pharmaceutical additives such as emulsifiers, surfactants, isotonic agents, pH adjustors can also be added. These pharmaceutically acceptable carriers and pharmaceutical additives are well-known in the field of pharmaceutical formulation and used widely.

Specific examples of diseases and disorders in cases where the agent is administered to a living body include, but not limited to, burns, decubituses, wounds, skin ulcers, leg ulcers, diabetic ulcers, occlusive arterial disease and arteriosclerosis obliterans. The angiogenesis-inducing agents of the present invention can be used as agents for the prevention, amelioration or treatment for these diseases or disorders. The polypeptides of the present invention have not only a high angiogenesis-inducing activity but also an antibacterial activity. Thus, since they have an antibacterial activity against Gram-positive bacteria such as *Staphylococcus aureus* (including methicillin-resistant *Staphylococcus aureus*), *Staphylococcus epidermidis*, and the like, and Gram-negative bacteria such as *Escherichia coli, Klebsiella pneumoniae*, enterobacteria, and the like, they are especially suited as an agent for the prevention, amelioration or treatment of diseases or disorders which is desired to have an antibacterial activity as well. Examples of such diseases or disorders include, among the above-mentioned diseases or disorders, burns, decubituses, wounds, skin ulcers, leg ulcers, diabetic ulcers.

In the present description, the term "skin wound" (sometimes referred to as simply "wound") refers to physical damage of body surface tissue which is caused by external and/or internal factors, and includes skin wounds caused by cut wounds, lacerations, stab wounds, bite wounds, gunshot wounds, contused wounds, abrasions, surgical wounds, erosions, burns, decubituses, intractable wounds, skin ulcers, leg ulcers, diabetic ulcers, occlusive arterial disease and arteriosclerosis obliterans.

The polypeptides of the present invention can be used for the treatment as an agent for treating a wound(s), an antibacterial agent, or an agent for preventing infection. All the peptides of SR-1 (SEQ ID NO:1), SR-2 (SEQ ID NO:2), SR-3 (SEQ ID NO:3), SR-4 (SEQ ID NO:4), SR-5 (SEQ ID NO:5) and SR-6 (SEQ ID NO:6), more preferably SR-1 and SR-3, especially preferably SR-1, can be used for the treatment. Each of the polypeptides of the present invention has two effects, i.e., an effect to heal and prevent infection and an effect to heal a wound(s), as one effective ingredient.

The polypeptides of the present invention can exhibit an effect to heal a wound(s) comparable to an effect of an agent containing bFGF as an effective ingredient (FIBLAST Spray (registered trademark), referred to herein as "bFGF formulation") which has already used as an agent for treating a wound(s). While bFGF does not have an antibacterial activity, the polypeptides of the present invention have an antibacterial activity. Therefore, the polypeptides of the present invention can be a therapeutic agent which is more effective for a skin wound(s) associated with infection. As described in the Examples below, the polypeptide of the present invention has an early healing effect in a wound(s) associated with infection, compared with the bFGF formulation. Although the effect of SR-1 polypeptide on a wound associated with *Staphylococcus aureus* infection is exemplified in the Examples of the present description, those skilled in the art can easily understand that polypeptides which can be used and the bacteria against which the polypeptide can exhibit the effect are not limited to the example, and that any of the polypeptides of the present invention also exhibits a similar effect against *Staphylococcus aureus* and other bacteria, especially the bacteria against which the polypeptides of the present invention exhibit antimicrobial properties, such as *Escherichia coli, Pseudomonas aeruginosa, Staphylococcus epidermidis, Klebsiella pneumoniae* and enterobacteria.

Furthermore, those skilled in the art can also easily understand that the polypeptides of the present invention prevent bacterial infection and exhibit an early healing effect as in the example, even when the polypeptides of the present invention have been administered to a wound(s) in which infection is not observed and then the wound(s) has(have) been brought into contact with bacteria.

Thus, the polypeptides of the present invention, preferably SR-1 and SR-3 polypeptides, especially SR-1 polypeptide, can be used for the treatment or amelioration of all the wounds which are not associated with infection, and further for the treatment or amelioration of all the wounds associated with infection, among all of skin wounds including skin wounds caused by cut wounds, surgical wounds, erosions, burns, decubituses, intractable wounds, skin ulcers, leg ulcers, diabetic ulcers, occlusive arterial disease and arteriosclerosis obliterans. These polypeptides have also an effect to prevent infection in a wound(s) which has(have) a possibility of infection. The term "treatment or amelioration of a wound(s)" includes healing of the wound(s), reduction of the degree of the wound(s), and suppression of the deterioration of a wound(s). Since the polypeptides of the present invention can prevent bacterial infection from occurring in a wound site, they can suppress the deterioration of the wound(s).

The term "erosion" is known to those skilled in the art and the meaning is as described in ordinary medical books. In other words, the term refers to skin damage which is caused by, for example, hydroa including impetigo contagiosa and pemphigus, a burn(s), and scratching in atopic dermatitis and which is within epidermis, and the condition wherein its surface after bullae occurring is wet. Also, the term "ulcer" is known to those skilled in the art and the meaning is as described in ordinary medical books. Briefly, the term refers to skin damage which reaches dermis or deeper tissue, and the wound that is deeper compared with erosions. Bleeding and/or exudate is/are often observed in ulcers. These ulcers may occur subsequent to diseases associated with hematogenous disorders including collagen disease, diabetes or vasculitis, malignant tumors, or the like. In addition, burn ulcers and pressure ulcers such as decubituses (bedsores) are also included. Even after their healing, scars called cicatrices often remain.

Consequently, these polypeptides have an effect for the treatment, amelioration or prevention against hard-to-heal wounds which are generally called intractable wounds. The intractable wounds include diabetic ulcers and crural ulcers, burn ulcers, decubituses (bedsores), pressure ulcers, necrosis, and the like. These ulcers and necrosis tend to be associated with bacterial infection, and the infection leads to their deterioration. Therefore, in the treatment or amelioration of these wounds, it is desirable that regeneration of skin tissue at their wound sites be enhanced after granulation and the prevention and treatment of bacterial infection also be carried out. If the polypeptides of the present invention are used as an agent for the prevention, amelioration or treatment of bacterial infection (including secondary infection) of a wound(s), an effect to prevent, ameliorate or treat infection will be obtained, and/or, due to the angiogenesis effect or wound healing effect which the polypeptides have, an effect to prevent, ameliorate or treat the wound(s) at an early stage will be also obtained.

Although the bacterial infection of the wound(s) is infection by various bacteria, examples of the bacteria include, in particular, *Staphylococcus aureus* (including methicillin-resistant *Staphylococcus aureus*), *Pseudomonas aeruginosa, Escherichia coli, Klebsiella pneumoniae*, and the like. It is therapeutically desirable that agents which have antimicrobial properties against these bacteria be administered after infection. However, on the other hand, it is also very useful in the treatment of a wound(s) that agents which have antimicrobial properties against these bacteria be administered before infection for the purpose of preventing infection.

Further, the polypeptides of the present invention are more desirable from a cosmetic standpoint, since cicatrices are less likely to remain compared with the bFGF formulation which is widely used as an agent for treating a wound(s).

While an angiogenesis-inducing agent, an antibacterial agent, an agent for treating a skin wound(s) or a prophylactic agent against skin wound infection of the present invention can be used individually, two or more of the polypeptides of the present invention can also be used in combination. In addition, if further antimicrobial properties are desired, they can be used in combination with other antibacterial agents or antibiotics. Examples of such antibacterial agents or antibiotics include cephem, carbapenem, aminoglycoside, new quinolone, β-lactam, penicillin and glycopeptide antibiotics and the like, and more particularly include ceftazidime, meropenem, tobramycin, ciprofloxacin, methicillin, ampicillin, vancomycin, and the like, but not limited thereto.

EXAMPLES

The present invention will now be described more concretely by way of Examples. However, the present invention is not limited to the Examples below.
1. Synthesis of the Polypeptides Protected peptide resins were synthesized by Fmoc method using a full-automatic solid-phase synthesizer according to the method described in documents such as Solid Phase Peptide Synthesis, Pierce (1984), Fmoc solid synthesis: a practical approach, Oxford University Press (2000) and The Fifth Series of Experimental Chemistry, Vol. 16, Synthesis of Organic Compounds IV. To the obtained protected peptide resins, trifluoroacetic acid (TFA) and a scavenger (a mixture of thioanisole, ethanedithiol, phenol, triisopropylsilane, water, etc.) were added to obtain crude peptides by cleaving from the resin and deprotecting. These crude peptides were purified by gradient elution using a reversed-phase HPLC column (ODS) in 0.1% TFA-H₂O/CH₃CN system. Fractions containing the desired substances were collected and freeze-dried to obtain the desired peptides. The amino acid sequences of the synthesized peptides were confirmed by using an amino acid sequencer G1000A (Hewlett Packard), PPSQ-23A (SHIMADZU CORPORATION) or ProciscLC (ABI). The sequences of the peptides are shown below. SR-2, SR-3, SR-4 and SR-6 were amidated at their C-termini.

SR-1
(SEQ ID NO: 1)
MLKLIFLHRLKRMRKRLKRK

SR-2
(SEQ ID NO: 2)
ELRFLHRLKRRLRKRLKRKLR-amide

SR-3
(SEQ ID NO: 3)
ELRFLHRLKRMRKRLKRKLR-amide

SR-4
(SEQ ID NO: 4)
KLIFLHRLKRMRKRLKRKLR-amide

SR-5
(SEQ ID NO: 5)
KRMRKRLKRKLRLWHRKRYK

SR-6
(SEQ ID NO: 6)
MRKRLKRKLRLWHRKRYK-amide

AG30-5C
(SEQ ID NO: 7)
MLKLIFLHRLKRMRKRLKRKLRFWHRKRYK

2. Analysis of the Polypeptides Using MALDI-TOF/MS

The sequences of the synthesized polypeptides were confirmed by the results of analysis using MALDI-TOF/MS. To 1 μL of a solution containing 0.1% polypeptide in TFA/50% acetonitrile, whose final concentration was 100 μg/mL, 1 μL of a matrix solution (α-Cyano 4-Hydroxy Cinnamic Acid) was added to obtain a measurement sample for MALDI. The measurement sample for MALDI (0.4 μL) was applied on a MALDI target plate and dried, followed by measurement using MALDI-TOF/MS.
MALDI-TOF/MS conditions:
Laser Intensity: 2100
Number of Laser Shots: 1000
Results The theoretical value and measured value of MALDI-TOF/MS for each polypeptide were shown in Table 1. The detected m/z of each polypeptide was matched to each theoretical value, and the sequences of the synthesized polypeptides were confirmed.

TABLE 1

| Polypeptide | MH+ (Da) | |
|---|---|---|
| | Theoretical value | Measured value |
| SR-1 | 2664.711405 | 2664.7424 |
| SR-2 | 2870.897365 | 2870.9932 |
| SR-3 | 2732.752685 | 2732.7961 |
| SR-4 | 2688.788005 | 2688.7334 |
| SR-5 | 2836.790145 | 2837.0413 |
| SR-6 | 2551.610055 | 2551.5486 |
| AG30-5C | 4135.558675 | 4135.9741 |

3. Angiogenesis-Inducing Activity of the Polypeptides

Using AG30-5C as a positive control, the angiogenesis-inducing activity of SR-1 and SR-2 was measured. More concretely, using an angiogenesis kit (Angiogenesis Kit, KZ-1000, KURABO INDUSTRIES LTD.), the ability of the polypeptides to form lumina was evaluated. As a negative control, polypeptide-free group (Control) was used.

Each polypeptide was added to a special medium for angiogenesis (KURABO INDUSTRIES LTD., KZ-1500) such that the concentration thereof was 10 μg/mL. Cells were cultured at 37° C. under 5% CO₂ in a 24-well plate using the special media to which the polypeptide was added. The medium was replaced with a medium containing the same polypeptide on day 4, day 7 and day 9 of culture. On day 11 from the beginning of the culture, the medium was removed and staining was performed using a kit for staining lumina (for CD31 antibody staining) according to the following procedure.

The primary antibody (mouse anti-human CD31 antibody) was 4000-fold diluted with a blocking solution (Dulbecco's phosphate buffered saline (PBS(−)) containing 1% BSA). To each well, 0.5 mL of this primary antibody solution was added, and the plate was incubated for 60 minutes at 37° C. After the completion of the incubation, each well was washed totally 3 times with 1 mL of the blocking solution.

Then, 0.5 mL of a secondary antibody solution (goat anti-mouse IgG/alkaline phosphatase conjugate) 500-fold diluted with the blocking solution was added to each well. The plate was incubated for 60 minutes at 37° C., and thereafter each well was washed 3 times with 1 mL of distilled water. During that period, 2 tablets of BCIP/NBT were dissolved into distilled water, and the obtained solution was filtered through a filter having a pore size of 0.2 μm to prepare a substrate solution. To each well, 0.5 mL of the prepared BCIP/NBT substrate solution was added, and the plate was incubated at 37° C. until the lumina turned to deep purple (typically for 5-10 minutes). After the completion of the incubation, each well was washed 3 times with 1 mL of distilled water. After washing, the washing solution was removed by aspiration, and the plate was left to stand and dry naturally. After drying, photographs of each well were taken under a microscope.

Each of the obtained images was quantified using an angiogenesis quantification software. Computer analysis was carried out on various parameters. And, on the basis of its scale, the lengths of formed lumina observed in each visual field were measured, and the effect of adding the polypeptides compared with Control was evaluated.

The results are shown in Table 2.

TABLE 2

| Polypeptide | The Length of Lumina (Percentage when taking Control as 100) |
|---|---|
| SR-1 | 124.3 |
| SR-2 | 124.6 |
| AG30-5C | 119.1 |

As shown in Table 2, both SR-1 and SR-2, which are the polypeptides of the present invention, individually had an angiogenesis-inducing activity. Their activity was higher than AG30-5C.

4. Antibacterial Activity of the Polypeptides (Part 1)

The antibacterial activity of the polypeptides was measured using an ATP assay method.

That is, using BacTiter-Glo Microbial Cell Viability Assay kit available from PROMEGA, the antibacterial activity of the peptides was evaluated from the viability of bacteria. In other words, ATP amount in viable bacteria in cases where the concentration of the peptides was 10 μg/mL was measured using a microtiter plate or test tubes.

With respect to the strains, *Staphylococcus aureus* ATCC29213 (*S. aureus* ATCC29213) as Gram-positive bacteria, or, alternatively, *Pseudomonas aeruginosa* (*P. aeruginosa* ATCC27853) as Gram-negative bacteria, was used. The bacteria were cultured in media for 3 to 4 hours, and thereafter absorbances at $A_{600}$ were measured. Bacterial suspensions were diluted with Mueller-Hinton broth (MHB) according to McFarland #0.5. Each strain was added so as to attain about 0.5–1×10$^5$ CFU/mL (final concentration) in terms of *Escherichia coli*. Each peptide was prepared and added to a microplate or test tubes so as to attain a final concentration of 10 μg/mL, and the bacterial suspension was added thereto. A solution to which the peptides were not added was considered as a negative control, and a solution to which tobramycin (TOB) was added was considered as a positive control. The plate was incubated at 37° C. for 3 hours, and the amount of ATP in the culture media was measured. Relative values were calculated by comparison with the negative control, and these values were regarded as the viability.

The results are shown in Table 3.

TABLE 3

| | Viability (%) | |
|---|---|---|
| Compound | *Staphylococcus aureus* | *Pseudomonas aeruginosa* |
| TOB | 3.5 | 1.8 |
| SR-1 | 21.9 | 31.0 |
| SR-2 | 8.0 | 4.2 |
| SR-3 | 11.2 | 9.3 |
| SR-4 | 2.1 | 13.2 |
| SR-6 | 16.2 | 20.2 |
| AG30-5C | 29.1 | 12.9 |

As shown in Table 3, SR-1, SR-2, SR-3, SR-4 and SR-6, which are the polypeptides of the present invention, individually had a higher antibacterial activity against *Staphylococcus aureus* than AG30-5C. Also, SR-2 and SR-3 individually had a higher antibacterial activity against *Pseudomonas aeruginosa* than AG30-5C.

5. Antibacterial Activity of the Polypeptides (Part 2)

Further, in order to prove the antibacterial activity of the above-described polypeptides, in addition to *Staphylococcus aureus* and *Pseudomonas aeruginosa* as mentioned above, the antibacterial activity against *Escherichia coli*, two types of enterobacteria (enterobacteria (1) and enterobacteria (2), respectively), *Klebsiella pneumoniae*, and *Staphylococcus epidermidis* was also measured.

ATP (%) of the antibacterial activity was measured in the same manner as mentioned above, and the "minimum inhibitory concentration (MIC)" was measured as follows. MIC is the lowest concentration of an agent that may inhibit the growth of a bacterium. MIC is used as a parameter for the efficacy of an antibacterial agent, for the strength of bacterial sensitivity, or the like. The bacteria can grow (proliferate) when the concentration is not higher than MIC, and cannot grow when the concentration is higher than MIC. Its measurement is carried out according to a method defined as a standard method by Japanese Society of Chemotherapy or CLINICAL AND LABORATORY STANDARD INSTITUTE (CLSI), but, in this Example, its measurement was carried out by a broth microdilution method in accordance with "M100-S17/M7-A7" (Performance Standards for Antimicrobial Susceptibility Testing; Seventeenth Informational Supplement, Vol. 27 No. 1) published by CLSI on January, 2007. That is, sensitivity test of agents was carried out using a microtiter plate or test tubes.

The bacteria were cultured in the liquid media for 4 to 6 hours, and thereafter absorbances at $A_{600}$ were measured. Bacterial suspensions were diluted with Mueller-Hinton broth (MHB) according to McFarland #0.5. Each strain was added so as to attain about 10$^5$ CFU/ml (final concentration). Each peptide was prepared to an optional concentration, and the solutions were serially diluted from the concentration. The polypeptide at each concentration stage was added to a microplate or test tubes, and the bacterial suspension was added thereto. A solution to which the peptide was not added was considered as a negative control, and solutions to which meropenem (MEPM), ciprofloxacin (CPFX), tobramycin (TOB), or oxacillin (OX) was individually added were considered as positive controls. The plate was incubated at 37° C. for 20 hours, the lowest concentration where bacterial growth was inhibited was regarded as the minimum inhibitory concentration.

With respect to each strain, *Escherichia coli*: ATCC 25922 (*Escherichia coli* ATCC 25922), *Pseudomonas aeruginosa*: ATCC 27853 (*Pseudomonas aeruginosa* ATCC 27853), *Staphylococcus aureus*: ATCC29213 (*Staphylococcus aureus* ATCC29213), *Klebsiella pneumoniae*: JCM 1662 (*Klebsiella pneumoniae* JCM 1662), enterobacteria (1): JCM 1232 (*Enterobacter cloacae* JCM 1232), enterobacteria (2): JCM 1235 (*Enterobacter aerogenes* JCM 1235), and *Staphylococcus epidermidis*: JCM 2414 (*Staphylococcus epidermidis* JCM 2414), were used.

For *Staphylococcus aureus*, *Pseudomonas aeruginosa*, *Escherichia coli*, and *Staphylococcus epidermidis*, the measurements by both MIC and ATP assay methods were carried out, but, for two types of Enterobacteria (Enterobacteria (1) and Enterobacteria (2), respectively) and *Klebsiella pneumoniae*, only ATP assay was carried out. As the concentrations of the agents in ATP assay, the concentrations as described in the Tables were used.

The results are shown in Table 4-1 and Table 4-2 (ATP activity) and Table 5 (MIC) below.

TABLE 5

Table of MIC

|   | Escherichia coli MIC (µg/mL) | Pseudomonas aeruginosa MIC (µg/mL) | Staphylococcus aureus MIC (µg/mL) | Staphylococcus epidermidis MIC (µg/mL) |
|---|---|---|---|---|
| TOB | 0.25-1.0 | 0.25-1.0 | 0.12-1.0 | 1 |
| CPFX | 0.004-0.015 | 0.25-1.0 | 0.12-0.5 | 0.12-0.5 |
| OX | — | — | 0.12-0.5 | 0.12-0.5 |
| MEPM | 0.008-0.06 | 0.25-1.0 | 0.03-0.12 | 0.125 |
| SR-1 | 64 | 32 | 16 | 128< |
| SR-5 | 64 | 128≤ | 32 | 8-16 |
| SR-4 | 32 | 32 | 16 | 8-32 |
| SR-2 | 16 | 8-32 | 16-32 | 8 |
| SR-3 | 16-32 | 16-32 | 16-32 | 8 |

From these results, it was proved that the polypeptides SR-1 to 5 individually had an antibacterial activity with respect to all of these bacteria.

6. Effect on Dermal Fibroblast Growth

Next, the effect of these polypeptides on the growth of human dermal fibroblasts (NHDF) was studied. A cell growth activity of the polypeptides was examined using Cell Counting Kit (WST-1) available from Dojindo Laboratories. As a negative control (Control), polypeptide-free group was used. Cells (normal human newborn foreskin dermal fibroblast: NHDF(NB)) were plated in a 96-well plate ($0.5 \times 10^4$ cells/well/1004, serum 1%). About 3 hours after plating the cells, the polypeptides (1, 3, 10, 30, or 100 µg/ml) and FGF (100 ng/ml) as a positive control were individually added thereto in an amount of 100 µL. To the unstimulated group, only a

TABLE 4-1

Table of ATP activity

| | Escherichia coli | | | Pseudomonas aeruginosa | | | Staphylococcus aureus | | | Staphylococcus epidermidis | | |
|---|---|---|---|---|---|---|---|---|---|---|---|---|
| | ATP assay concentration (µg/ml) | ATP (%) mean | S.D. | ATP assay concentration (µg/ml) | ATP (%) mean | S.D. | ATP assay concentration (µg/ml) | ATP (%) mean | S.D. | ATP assay concentration (µg/ml) | ATP (%) mean | S.D. |
| TOB | 1.0 | 3.8 | 0.2 | 1.0 | 1.7 | 0.2 | 1.0 | 3.1 | 0.6 | 1.0 | 4.2 | 0.2 |
| CPFX | 0.015 | 15.4 | 1.1 | 1.0 | 2.3 | 0.16 | 0.5 | — | — | 0.5 | 7.3 | 0.5 |
| OX | 0.5 | 114.4 | 24.3 | 0.5 | 83.1 | 9.0 | 0.5 | 72.8 | 41.2 | 0.5 | 101.4 | 3.1 |
| MEPM | 0.1 | 15.7 | 0.6 | 1.0 | 20.2 | 4.3 | 0.12 | — | — | 0.125 | 28.2 | 1.5 |
| SR-1 | 10 | 18.4 | 0.7 | 10 | 26.0 | 21.0 | 10 | 5.2 | 4.6 | 10 | 5.2 | 0.4 |
| SR-5 | 10 | 27.0 | 1.5 | 10 | 16.4 | 6.6 | 10 | 24.2 | 0.3 | 10 | 3.6 | 0.1 |
| SR-4 | 10 | 13.0 | 0.7 | 10 | 9.8 | 5.8 | 10 | 1.0 | 0.4 | 10 | 5.5 | 0.2 |
| SR-2 | 10 | 6.2 | 0.9 | 10 | 1.0 | 0.5 | 10 | 4.4 | 2.2 | 10 | 2.6 | 0.2 |
| SR-3 | 10 | 16.5 | 0.6 | 10 | 3.3 | 2.4 | 10 | 3.5 | 0.1 | 10 | 4.1 | 0.1 |

TABLE 4-2

Table of ATP activity

| | Klebsiella pneumoniae | | | Enterobacteria (1) | | | Enterobacteria (2) | | |
|---|---|---|---|---|---|---|---|---|---|
| | ATP assay concentration (µg/ml) | ATP (%) mean | S.D. | ATP assay concentration (µg/ml) | ATP (%) mean | S.D. | ATP assay concentration (µg/ml) | ATP (%) mean | S.D. |
| TOB | 4.0 | 3.8 | 0.1 | 4.0 | 3.0 | 0.2 | 4.0 | 0.5 | 0.1 |
| CPFX | 1.0 | 8.2 | 0.6 | 1.0 | 3.1 | 0.2 | 1.0 | 3.2 | 0.1 |
| OX | 0.5 | 142.2 | 11.1 | 4.0 | 97.7 | 6.0 | 4.0 | 86.9 | 11.7 |
| MEPM | 8.0 | 11.9 | 0.5 | 8.0 | 5.6 | 0.5 | 8.0 | 2.3 | 0.1 |
| SR-1 | 10 | 22.1 | 1.4 | 10 | 4.9 | 0.5 | 10 | 39.4 | 0.9 |
| SR-5 | 10 | 30.0 | 2.8 | 10 | 3.4 | 0.1 | 10 | 41.5 | 1.6 |
| SR-4 | 10 | 15.0 | 0.8 | 10 | 4.9 | 0.6 | 10 | 20.9 | 0.6 |
| SR-2 | 10 | 9.1 | 0.6 | 10 | 3.0 | 0.1 | 10 | 15.3 | 0.7 |
| SR-3 | 10 | 20.3 | 1.3 | 10 | 4.3 | 0.3 | 10 | 23.5 | 1.0 | medium was added in an amount of 100 μL. The plate was left to stand in a $CO_2$ incubator for about 48 hours. Thereafter, WST-1 agent was added to each well in an amount of 20 μL, and then the plate was left to stand in a $CO_2$ incubator for about 2 hours. Absorbances at wavelengths of 450 nm and 620 nm were measured using Wallac 1420 ARVOsx (Program: WST-1). A value of $O.D._{450}-O.D._{620}$ was calculated for each measurement. The values obtained by subtracting the average of values of $O.D._{450}-O.D._{620}$ of blank wells which did not contain cells from values of $O.D._{450}-O.D._{620}$ of the measured wells were regarded as Net $O.D._{450}$. The cell growth activity was evaluated on the basis of the ratio of Net $O.D._{450}$ of polypeptide-containing groups relative to Net $O.D._{450}$ of the unstimulated group.

The results are shown in FIG. 1. As shown in FIG. 1, all the peptides exhibited a growth-promoting effect on fibroblast cells at a concentration from 1 μg/ml to 30 μg/ml, but tended to exhibit toxicity on the cells at a concentration of 100 μg/ml.

7. Lumen Formation

Using an angiogenesis kit available from KURABO INDUSTRIES LTD. (Product No.: KZ-1000), lumen formation by the polypeptides was evaluated. Vascular endothelial growth factor A (VEGF-A) as a positive control, and polypeptide-free, unstimulated group as a negative control, were used.

Using a special medium for angiogenesis which was attached to the kit, each polypeptide was prepared such that the concentration thereof was respectively 0.5, 2.5 and 10 μg/mL. To a 24-well plate in which cells were plated (the cells were those obtained by co-culturing human vascular endothelial cells and fibroblast cells at an optimum concentration) which was attached to the kit, the special medium for angiogenesis containing each polypeptide was added, and the cells were cultured at 37° C. under 5% $CO_2$. The medium was replaced with a medium containing the same additive on day 4, day 7 and day 9 of culture. On day 11 from the beginning of the culture, staining was performed using a kit for staining lumina (for CD31 antibody staining) according to the following procedure.

The media were removed, and washing was performed with Dulbecco's phosphate buffered saline (PBS(−)). Thereafter, ice-cooled 70% ethanol was added to the plate, and the cells were fixed. Each well was washed with a blocking solution (Dulbecco's phosphate buffered saline (PBS(−)) containing 1% BSA). To each well, 0.5 mL of the primary antibody for CD31 staining (mouse anti-human CD31 antibody) 4000-fold diluted with the blocking solution was added, and then the plate was incubated for 60 minutes at 37° C. After the completion of the incubation, each well was washed totally 3 times with 1 mL of the blocking solution. Then, 0.5 mL of the secondary antibody solution (goat anti-mouse IgG/alkaline phosphatase conjugate) 500-fold diluted with the blocking solution was added to each well. The plate was incubated for 60 minutes at 37° C., and thereafter each well was washed 3 times with 1 mL of distilled water. During that period, 2 tablets of BCIP/NBT were dissolved into distilled water, and the obtained solution was filtered through a filter having a pore size of 0.2 μM to prepare a substrate solution. To each well, 0.5 mL of the prepared BCIP/NBT substrate solution was added, and the plate was incubated at 37° C. until the lumina turned to deep purple (typically for 5-10 minutes). After the completion of the incubation, each well was washed 3 times with 1 mL of distilled water. After washing, the washing solution was removed by aspiration, and the plate was left to stand and dry naturally. After drying, photographs of each well were taken under a microscope.

Each of the obtained images was quantified using an angiogenesis quantification software. The area and length of formed lumina observed in each visual field were measured on the basis of the scale of an angiogenesis quantification software available from KURABO INDUSTRIES LTD. (angiogenesis quantification software Ver 1.0), and evaluated on the basis of the ratio of the area or length of polypeptide-containing groups relative to the area or length of the negative control group.

The results are shown in Table 6-1 (the area of lumina) and Table 6-2 (the length of lumina) below. In Table 6-1 and Table 6-2, relative values when taking the negative control as 100 are shown.

TABLE 6-1

The Area of Lumina

| Polypeptide | Polypeptide concentration (μg/mL) | | |
|---|---|---|---|
| | 0.5 | 2.5 | 10 |
| SR-1 | 94.6 | 132.3 | 156.6 |
| SR-2 | 110.7 | 138.4 | 138.0 |
| SR-3 | 100.8 | 111.3 | 118.0 |
| SR-4 | 90.5 | 104.6 | 96.2 |
| SR-5 | 103.4 | 93.6 | 107.7 |
| SR-6 | 97.3 | 104.5 | 98.6 |
| VEGF-A | | 189.2 | |

TABLE 6-2

The Length of Lumina

| Polypeptide | Polypeptide concentration (μg/mL) | | |
|---|---|---|---|
| | 0.5 | 2.5 | 10 |
| SR-1 | 97.4 | 130.5 | 149.5 |
| SR-2 | 108.9 | 134.9 | 129.9 |
| SR-3 | 101.9 | 115.3 | 122.6 |
| SR-4 | 97.0 | 103.2 | 96.4 |
| SR-5 | 106.2 | 95.0 | 106.8 |
| SR-6 | 98.4 | 98.2 | 96.6 |
| VEGF-A | | 169.8 | |

From these results, it was shown that SR-1, SR-2 and SR-3 polypeptides clearly have a high ability to form lumina.

8. Stability

Then, the stability of five polypeptides SR-1 to 5 in serum was evaluated.

In human serum (purchased from KAC Co., Ltd.), or in rat serum obtained by collecting blood from a rat, then leaving the collected blood to stand at room temperature followed by centrifugation, each of the peptides was dissolved so as to attain a final concentration of 500 μg/mL, and the obtained solutions were left to stand at 37° C. After leaving to stand for 10 min or 30 min or 60 min, these solutions were subjected to HPLC chromatogram analysis to detect peaks of the decomposition products, and calculate the ratio of the concentration of the peptides which remained in the solutions relative to the starting concentration. In addition, the half-lives of the peptides in serum were also calculated.

HPLC chromatogram analysis conditions are as follows.
Column: CAPCELL PAK C18 MGII (S-3 μm, 4.6×150PE, Shiseido Co., Ltd.)
Guard Column: GUARD CARTRIDGE CAPCELL C18 MG (S-3 μm, 4.0×10PE, Shiseido Co., Ltd.)
Column temperature: 50° C.
Mobile phase A: 0.025% trifluoroacetic acid solution
Mobile phase B: 0.025% trifluoroacetic acid-acetonitrile
Flow Rate: 1.0 mL/min
Detector: an ultraviolet absorptiometer (Measurement Wavelength: 220 nm)
Injection volume: 100 μL
Gradient conditions:

TABLE 7

| Time (min) | Mobile phase A (%) | Mobile phase B (%) |
|---|---|---|
| 0 | 100 | 0 |
| 1 | 100 | 0 |
| 15 | 55 | 45 |
| 20 | 55 | 45 |
| 20.1 | 100 | 0 |
| 25 | 100 | 0 |

The results are shown in Table 8 below.

TABLE 8

Stability in rat serum

| Peptide | Peptide-remaining ratio (%) | | | | Half-life (min) |
|---|---|---|---|---|---|
| | 0 min | 10 min | 30 min | 60 min | |
| SR-1 | 100 | — | 0 | 0 | 3 |
| SR-2 | 100 | 69 | — | 51.7 | 75 |
| SR-3 | 100 | 53 | — | 44.4 | 67 |
| SR-4 | 100 | — | 95 | 64.5 | 95 |
| SR-5 | 100 | — | 0 | 0 | 4 |

TABLE 9

Stability in human serum

| Peptide | Peptide-remaining ratio (%) | | | Half-life (min) |
|---|---|---|---|---|
| | 0 min | 10 min | 60 min | |
| SR-1 | 100 | 0 | 0 | 4 |
| SR-2 | 100 | 98 | 3.4 | 12 |
| SR-3 | 100 | 79 | 6.8 | 15 |
| SR-4 | 100 | 69 | 8 | 16 |
| SR-5 | 100 | 25 | 9.5 | 21 |

In rat serum, SR-1 and SR-5 were completely decomposed within 1 hour, but the decomposition of SR-2, SR-3 and SR-4 was confined to the range from 35 to 55% at 37° C. and 1 hour. In human serum, more than 90% of any of the peptides were decomposed within 1 hour.

Further, the stability of each polypeptide (SR-1 to 5) in PBS was also evaluated. Solutions of the peptides in PBS, whose final concentration was 1 mg/mL, were stored at 4° C. and room temperature. Immediately after preparing, and 2 and 4 weeks after preparation, the solutions were subjected to HPLC analysis in the same conditions as described above except that the injection volume was 5 μL. And the storage stability in solution was evaluated on the basis whether peaks of the decomposition products were observed or not. As a result, decomposition products were not observed, and it was found that all the polypeptides have a sufficient storage stability in PBS both at room temperature and at 4° C.

9. Comparison of the Ability to Form Granulation Tissue in Paper Disc Model

Then, the ability to form granulation tissue of five polypeptides SR-1 to 5 in vivo was studied. Each of the peptides which were test substances and whose concentration was respectively 25, 250 and 2500 μg/mL, the bFGF formulation (positive controls) whose concentration was respectively 2.5, 25 and 250 μg/mL, or saline (negative controls) was added to a paper disc (FILTER PAPER φ8 mm, ADVANTEC) in an amount of 40 μl, such that, in the final state, the dosage of each peptide was 1, 10 or 100 μg/disc and the dosage of the bFGF formulation was 0.1, 1 or 10 μg/disc. The prepared paper discs were embedded subcutaneously into the back of Crl:CD (SD) rats (male, 9-week old, obtained from Charles River Laboratories Japan, Inc.). Eight days later, the paper discs were taken out, and the granulation tissues around the paper discs were collected to determine their wet weight.

The results are shown in FIGS. 2A to 2F. With respect to SR-1 and SR-3, when their dosage was 10 μg/disc (250 μg/mL×40 μl/disc), the largest increase in the granulation tissue weight was observed. From this result, it is thought that especially SR-1 and SR-3 also promote angiogenesis in topical administration in vivo, and contribute to form granulation tissue.

9. Effect to Heal Cut Wounds

Next, using rat cut-wound model, the effect of the five polypeptides SR-1 to 5 to heal cut wounds in vivo was evaluated. As described in Tetsuaki Yamaura et al. (Oyo Yakuri (Pharmacometrics) 22, 565-579 (1981)), the rat cut-wound model was produced and the wound closing tension was measured.

That is, a cut wound of 30 to 36 mm was made on the back of Crl:CD (SD) rats (male, 7-week old, obtained from Charles River Laboratories Japan, Inc.) using a safety razor, and sutured at 3 points equally spaced. The day when this surgical treatment was applied was regarded as day 1 (day 0). Onto the suture site, 50 μL of each of the peptides which were test substances and were respectively prepared to the concentration of 10, 100 and 1000 μg/mL was added dropwise (the added amounts were 500 ng and 5 and 50 μg, respectively). Additions of 50 μL physiological saline were regarded as negative controls (Saline). Each peptide was added dropwise once a day till the day when the measurement of the wound closing tension was carried out. The sutures were removed day 3, and the wound closing tension was measured on day 6.

The results are shown in FIGS. 3A to 3F. SR-1, SR-3, SR-4 and SR-5 exhibited an effect of increasing the wound closing tension. Compared with the healing of cut wounds of individuals to which the bFGF formulation was administered, in individuals to which any of the polypeptides of the present invention, especially SR-1, SR-2, SR-3 and SR-4, was administered, scars of cut wounds obviously had completely disappeared compared with individuals to which the bFGF formulation was administered, and the cicatrization was hardly observed by visual observation (data not shown).

10. Healing Effect of SR-1 in Rat Infected-Wound Model

While an effect to promote the healing of a cut wound was proved in the preceding section, in addition to that, a healing effect on a wound infected with *Staphylococcus aureus* was evaluated. Referring to Stenberg B D et al. (J Surg Res. 1991 January; 50(1):47-50.) and Hayward P et al. (Am J. Surg. 1992 March; 163(3):288-93.), a rat infected-wound model was produced as described below. HWY/slc hairless rats (male, 7-week old, obtained from Japan SLC, Inc.) were used. The day before full-thickness defects were created, the number of leukocytes was measured and cyclophosphamide was administered in tail vein (100 mg/kg). On the next day, the number of leukocytes was counted. Only the individuals in which the number of leukocytes was not more than 5000, were used. A square-shaped full-thickness defects of 1.73× 1.73 cm (about 3 cm²) were created on the back of the rats, and 25 µL of *Staphylococcus aureus* (about 10⁵ CFU/25 µL) and SR-1 peptide as a test substance (2 mg/mL) was added onto the defect sites (the administered amount was 50 µg). On the other hand, 25 µL of the bFGF formulation (3 µg/25 µL) was added dropwise in the bFGF formulation (a positive control) group, and 25 µL of physiological saline was added dropwise in the negative control groups. After administering the test substances, the wound sites were covered with a covering (PERME-ROLL, Nitto Medical Corporation) (day 0). Thereafter, *Staphylococcus aureus* and the test substance was added dropwise once a day for 4 consecutive days (days 0, 1, 2 and 3). Six days after the full-thickness defects were created (day 6), the area where the wounds had still not healed was measured to calculate the ratio of it relative to the area where the wounds were created, and the ratio was regarded as the wound area ratio on day 6.

The results are shown in Table 10 below.

TABLE 10

| Groups | Wound area ratio on day 6 |
| --- | --- |
| Ctl. (saline, uninfected) | 84.5 |
| Ctl. (saline, infected) | 96.4 |
| The bFGF formulation (infected) | 93.1 |
| SR-1 (infected) | 80.2 |

As shown in Table 10, in the groups where infection was induced in the wounds, the healing of the wounds was delayed compared with the uninfected group. It was also found that, in the group where SR-1 was administered to the infected wound, the wound epidermis was decreased more rapidly and the wound healed more quickly compared with the case where the bFGF formulation was administered to the infected wound. An efficacy equal to or greater than the bFGF formulation was observed. From these, it was proved that, with respect to wounds associated with infection, SR-1 exhibits a higher healing effect compared with the bFGF formulation.

INDUSTRIAL APPLICABILITY

The polypeptides of the present invention are useful as an angiogenesis-inducing agent, an antibacterial agent, an agent for the prevention, amelioration or treatment of a skin wound(s), and an agent for the prevention, amelioration or treatment of bacterial infection in a skin wound(s).

SEQUENCE LISTING FREE TEXT

[SEQ ID NO:1] SR-1
[SEQ ID NO:2] SR-2. Its arginine residue at the C-terminus is modified by amidation.
[SEQ ID NO:3] SR-3. Its arginine residue at the C-terminus is modified by amidation.
[SEQ ID NO:4] SR-4. Its arginine residue at the C-terminus is modified by amidation.
[SEQ ID NO:5] SR-5
[SEQ ID NO:6] SR-6. Its lysine residue at the C-terminus is modified by amidation.
Sequence Listing

The invention claimed is:

1. A polypeptide consisting of the amino acid sequence of any one of SEQ ID NO: 1-SEQ ID NO: 6.

2. A composition comprising the polypeptide of claim 1 and one or more pharmaceutically acceptable carriers.

3. The composition of claim 2, wherein said composition is in the form of a solution, emulsion, suspension, dust, powder, granule, gel, ointment, or transdermal patch.

4. The polypeptide of claim 1, wherein said polypeptide has angiogenesis-inducing activity; and the amino acid sequence of said polypeptide consists of the amino acid sequence of SEQ ID NO: 1.

5. The polypeptide of claim 1, wherein said polypeptide has angiogenesis-inducing activity; and the amino acid sequence of said polypeptide consists of the amino acid sequence of SEQ ID NO: 2.

6. The polypeptide of claim 1, wherein said polypeptide has angiogenesis-inducing activity; and the amino acid sequence of said polypeptide consists of the amino acid sequence of SEQ ID NO: 3.

7. The polypeptide of claim 1, wherein said polypeptide has angiogenesis-inducing activity; and the amino acid sequence of said polypeptide consists of the amino acid sequence of SEQ ID NO: 4.

8. The polypeptide of claim 1, wherein said polypeptide has angiogenesis-inducing activity; and the amino acid sequence of said polypeptide consists of the amino acid sequence of SEQ ID NO: 5.

9. The polypeptide of claim 1, wherein said polypeptide has angiogenesis-inducing activity; and the amino acid sequence of said polypeptide consists of the amino acid sequence of SEQ ID NO: 6.

10. A modified polypeptide consisting of the amino acid sequence of any one of SEQ ID NO: 1-SEQ ID NO: 6, wherein said polypeptide further comprises at least one chemical modification to increase its stability in vivo, said chemical modification being selected from the group consisting of:
  a) addition of PEG to said polypeptide wherein said PEG has a molecular weight of 3000-7000;
  b) substitution of the D-isomer for the corresponding L-isomer at one or more positions in the polypeptide amino acid sequence and wherein, apart from the presence of D-isomeric forms of amino acids, the sequence of said polypeptide consists of the sequence of any one of SEQ ID NO: 1-SEQ ID NO: 6;
  c) an acetylated N-terminus and/or an amidated C-terminus.

11. The polypeptide of claim 10, wherein said chemical modification comprises addition of PEG to said polypeptide wherein said PEG has a molecular weight of 3000-7000.

12. The polypeptide of claim 10, wherein said chemical modification comprises substitution of the D-isomer for the corresponding L-isomer at one or more positions in the polypeptide amino acid sequence and wherein, apart from the presence of D-isomeric forms of amino acids, the sequence of said polypeptide consists of the sequence of any one of SEQ ID NO: 1-SEQ ID NO: 6.

13. The polypeptide of claim 10, wherein said chemical modification comprises an acetylated N-terminus and/or an amidated C-terminus.

14. A composition comprising the polypeptide of claim 10 and one or more pharmaceutically acceptable carriers.

15. A modified polypeptide consisting of the amino acid sequence of SEQ ID NO: 1, wherein said polypeptide further comprises at least one chemical modification to increase its stability in vivo, said chemical modification being selected from the group consisting of:
  a) addition of PEG to said polypeptide wherein said PEG has a molecular weight of 3000-7000;
  b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 1;
  c) an acetylated N-terminus and/or an amidated C-terminus.

16. A modified polypeptide consisting of the amino acid sequence of SEQ ID NO: 2, wherein said polypeptide further comprises at least one chemical modification to increase its stability in vivo, said chemical modification being selected from the group consisting of:
  a) addition of PEG to said polypeptide wherein said PEG has a molecular weight of 3000-7000;
  b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 2;
  c) an acetylated N-terminus and/or an amidated C-terminus.

17. A modified polypeptide consisting of the amino acid sequence of SEQ ID NO: 3, wherein said polypeptide further comprises at least one chemical modification to increase its stability in vivo, said chemical modification being selected from the group consisting of:

a) addition of PEG to said polypeptide wherein said PEG has a molecular weight of 3000-7000;
b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 3;
c) an acetylated N-terminus and/or an amidated C-terminus.

18. A modified polypeptide consisting of the amino acid sequence of SEQ ID NO: 4, wherein said polypeptide further comprises at least one chemical modification to increase its stability in vivo, said chemical modification being selected from the group consisting of:
a) addition of PEG to said polypeptide wherein said PEG has a molecular weight of 3000-7000;
b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 4;
c) an acetylated N-terminus and/or an amidated C-terminus.

19. A modified polypeptide consisting of the amino acid sequence of SEQ ID NO: 5, wherein said polypeptide further comprises at least one chemical modification to increase its stability in vivo, said chemical modification being selected from the group consisting of:
a) addition of PEG to said polypeptide wherein said PEG has a molecular weight of 3000-7000;
b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 5;
c) an acetylated N-terminus and/or an amidated C-terminus.

20. A modified polypeptide consisting of the amino acid sequence of SEQ ID NO: 6, wherein said polypeptide further comprises at least one modification to increase its stability in vivo, said chemical modification being selected from the group consisting of:
a) addition of PEG to said polypeptide wherein said PEG has a molecular weight of 3000-7000;
b) substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of SEQ ID NO: 6;
c) an acetylated N-terminus and/or an amidated C-terminus.

21. A method for inducing angiogenesis in a mammal, comprising administering to said mammal an effective amount of the polypeptide of claim 1.

22. The method of claim 21, wherein said polypeptide is administered as a treatment for a skin wound or to treat bacterial infection in a skin wound.

23. The method of claim 22, wherein said skin wound is a cut, surgical wound, burn, intractable wound, skin ulcer, leg ulcer, diabetic ulcer, or an ulcer associated with occlusive arterial disease or arteriosclerosis obliterans.

24. The method of claim 22, wherein said polypeptide is administered topically as part of a solution, emulsion, suspension, dust, powder, granule, gel, ointment, or transdermal patch.

25. A method for inducing angiogenesis in a mammal, comprising administering to said mammal an effective amount of the polypeptide of claim 10.

26. A method for inducing angiogensis in a mammal, comprising administering to said mammal an effective amount of a polypeptide consisting of the amino acid sequence of SEQ ID NO: 1, 2, or 3, wherein said polypeptide optionally comprises a chemical modification selected from the group consisting of PEG added to said polypeptide wherein said PEG has a molecular weight of 3000-7000; an acetylated N-terminus; and an amidated C-terminus.

27. A method for inducing angiogensis in a mammal, comprising administering to said mammal an effective amount of a polypeptide consisting of the amino acid sequence of SEQ ID NO: 4, 5, or 6, wherein said polypeptide optionally comprises a chemical modification selected from the group consisting of PEG added to said polypeptide wherein said PEG has a molecular weight of 3000-7000; an acetylated N-terminus; and an amidated C-terminus.

28. The method of claim 25, wherein said chemical modification comprises substitution of the D-isomer for the corresponding L-isomer at one or more positions in the polypeptide amino acid sequence and wherein, apart from the presence of D-isomeric forms of amino acids, the sequence of said polypeptide consists of the amino acid sequence of any one of SEQ ID NO: 1-SEQ ID NO: 6.

29. The method of claim 25, wherein said chemical modification comprises an acetylated N-terminus or an amidated C-terminus.

* * * * *